United States Patent
Craighead et al.

(10) Patent No.: US 12,065,640 B2
(45) Date of Patent: *Aug. 20, 2024

(54) MICROFLUIDIC DEVICE FOR EXTRACTING, ISOLATING, AND ANALYZING DNA FROM CELLS

(71) Applicant: CORNELL UNIVERSITY, Ithaca, NY (US)

(72) Inventors: Harold G. Craighead, Ithaca, NY (US); Juraj Topolancik, San Jose, CA (US); Harvey Tian, Fayetteville, AR (US); Christopher Wallin, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 704 days.

This patent is subject to a terminal disclaimer.

(21) Appl. No.: 17/194,253

(22) Filed: Mar. 6, 2021

(65) Prior Publication Data

US 2021/0189381 A1    Jun. 24, 2021

Related U.S. Application Data

(63) Continuation of application No. 15/936,349, filed on Mar. 26, 2018, now Pat. No. 10,947,528, which is a
(Continued)

(51) Int. Cl.
*C12N 15/10* (2006.01)
*B01L 3/00* (2006.01)
(Continued)

(52) U.S. Cl.
CPC .... *C12N 15/1017* (2013.01); *B01L 3/502761* (2013.01); *C12M 47/10* (2013.01);
(Continued)

(58) Field of Classification Search
None
See application file for complete search history.

(56) References Cited

U.S. PATENT DOCUMENTS

| | | |
|---|---|---|
| 5,304,487 A | 4/1994 | Wilding et al. |
| 6,696,022 B1 | 2/2004 | Chan et al. |

(Continued)

FOREIGN PATENT DOCUMENTS

| | | |
|---|---|---|
| EP | 2714884 A1 | 4/2014 |
| WO | 2007050040 A1 | 5/2007 |

(Continued)

OTHER PUBLICATIONS

Schiro et al; Electrophoresis, vol. 28, pp. 2430-2438, published 2007.*

(Continued)

*Primary Examiner* — Robert T. Crow
(74) *Attorney, Agent, or Firm* — FisherBroyles, LLP; Andrew K. Gonsalves

(57) ABSTRACT

The present invention relates to a microfluidic device for extracting and isolating DNA from cells. The device includes a support having an inlet port for receiving a sample containing a cell, an outlet port for dispensing DNA isolated from the cell, and a microfluidic channel disposed within the support and extending from the inlet port to the outlet port. The microfluidic channel includes a micropillar array, an inflow channel disposed between the inlet port and the micropillar array, and an outflow channel disposed between the micropillar array and the outlet port. The micropillar array includes micropillars spatially configured to entrap, by size exclusion, the cell, to immobilize DNA released from the cell, and to maintain the immobilized DNA in elongated or non-elongated form when hydrodynamic force is applied (Continued)

INPUT CHANNEL WIDTH: 50-100μm
CHANNEL DEPTH: 20μm
CELL CAPTURE REGION WIDTH: 200-500μm
CHANNEL LENGTH: 13mm
MICROPILLAR WIDTH: 4μm
SMALLEST GAP BETWEEN PILLARS: 1.5μm to the microfluidic channel. Systems and methods of making and using the device are also provided herein.

10 Claims, 10 Drawing Sheets

Related U.S. Application Data continuation of application No. 14/124,479, filed as application No. PCT/US2012/041136 on Jun. 6, 2012, now Pat. No. 9,926,552.

(60) Provisional application No. 61/548,896, filed on Oct. 19, 2011, provisional application No. 61/493,748, filed on Jun. 6, 2011.

(51) Int. Cl.
   *C12M 1/00*     (2006.01)
   *C12Q 1/6806*   (2018.01)

(52) U.S. Cl.
   CPC .... *C12Q 1/6806* (2013.01); *B01L 2200/0663* (2013.01); *B01L 2400/0415* (2013.01); *B01L 2400/0487* (2013.01); *B01L 2400/086* (2013.01); *Y10T 29/49826* (2015.01)

(56) References Cited

U.S. PATENT DOCUMENTS

| | | |
|---|---|---|
| 6,977,148 B2 | 12/2005 | Dean et al. |
| 7,384,561 B2 | 6/2008 | Utsunomiya |
| 7,964,978 B1 | 6/2011 | Lee et al. |
| 8,562,918 B2 | 10/2013 | Jovanovich et al. |
| 8,871,446 B2 | 10/2014 | Hong et al. |
| 9,086,406 B2 | 7/2015 | Lee et al. |
| 9,128,091 B2 | 9/2015 | Toner et al. |
| 9,250,242 B2 | 2/2016 | Martin et al. |
| 9,506,845 B2 | 11/2016 | Fowler et al. |
| 9,803,192 B2 | 10/2017 | Craighead et al. |
| 9,926,552 B2 | 3/2018 | Craighead et al. |
| 10,947,528 B2 * | 3/2021 | Craighead ......... B01L 3/502761 |
| 2002/0081744 A1 | 6/2002 | Chan et al. |
| 2002/0125192 A1 | 9/2002 | Lopez et al. |
| 2003/0143599 A1 | 7/2003 | Makarov et al. |
| 2003/0162181 A1 | 8/2003 | Yang et al. |
| 2004/0050700 A1 | 3/2004 | Lopez-Canovas et al. |
| 2004/0053403 A1 | 3/2004 | Jedrzejewski et al. |
| 2004/0142491 A1 | 7/2004 | Indermuhle et al. |
| 2005/0019819 A1 | 1/2005 | Tooke et al. |
| 2005/0064575 A1 | 3/2005 | Belgrader et al. |
| 2005/0069459 A1 | 3/2005 | Ahn et al. |
| 2006/0133957 A1 | 6/2006 | Knapp et al. |
| 2007/0077547 A1 | 4/2007 | Shvets et al. |
| 2008/0124721 A1 | 5/2008 | Fuchs et al. |
| 2008/0124779 A1 | 5/2008 | Oh et al. |
| 2008/0125330 A1 | 5/2008 | Cady et al. |
| 2008/0160602 A1 | 6/2008 | He et al. |
| 2008/0274905 A1 | 11/2008 | Greene |
| 2009/0098541 A1 | 4/2009 | Southern et al. |
| 2009/0186776 A1 | 7/2009 | Webb et al. |
| 2009/0191563 A1 | 7/2009 | Steemers et al. |
| 2010/0047924 A1 | 2/2010 | Webster et al. |
| 2010/0137163 A1 | 6/2010 | Link et al. |
| 2010/0190146 A1 | 7/2010 | Bynum et al. |
| 2011/0014605 A1 | 1/2011 | Stone |
| 2011/0027873 A1 | 2/2011 | Cho et al. |
| 2011/0212440 A1 | 9/2011 | Viovy et al. |
| 2011/0301058 A1 | 12/2011 | Cheng et al. |
| 2012/0091235 A1 | 4/2012 | Li et al. |
| 2014/0154703 A1 | 6/2014 | Skelley et al. |
| 2014/0193812 A1 | 7/2014 | Hamilton et al. |
| 2014/0194313 A1 | 7/2014 | Craighead et al. |
| 2015/0018226 A1 | 1/2015 | Hansen et al. |
| 2015/0099642 A1 | 4/2015 | Barany et al. |
| 2015/0166987 A1 | 6/2015 | Craighead et al. |
| 2018/0305682 A1 | 10/2018 | Craighead et al. |

FOREIGN PATENT DOCUMENTS

| | | |
|---|---|---|
| WO | 2011017677 A2 | 2/2011 |
| WO | 2011017681 A2 | 2/2011 |
| WO | 2011038241 A1 | 3/2011 |
| WO | 2012162779 A1 | 12/2012 |
| WO | 2014153071 A1 | 9/2014 |
| WO | 2015077441 A2 | 5/2015 |
| WO | 2016154302 A1 | 9/2016 |
| WO | 2017004463 A1 | 1/2017 |
| WO | 2017205267 A1 | 11/2017 |
| WO | 2017205304 A1 | 11/2017 |

OTHER PUBLICATIONS

Cross et al, "Micro- and Nanofluidics for Biological Separations," in Lee, H., Westervelt, R.M., Ham, D. (eds) CMOS Biotechnology. Series on Integrated Circuits and Systems, Chapter 3, pp. 31-75,. Springer, Boston, MA. (Year: 2007).*

Turner et al, Phys. Rev. Letters, vol. 88, pp. 128103-1 to 128103-4. (Year: 2002).*

Zhang et al., "Aptamers selected by cell-SELEX for application in cancer studies," Bioanalysis, 2(5):907-918 (2010).

Dickey et al., "Oligonucleotide aptamers: A next-generation technology for the capture and detection of circulating tumor cells," Methods, 97:94-103 (2016).

Wan et al., "Capture, isolation and release of cancer cells with aptamer-functionalized glass bead array," Lab Chip, 12:4693-4701 (2012).

Phillips et al., "Enrichment of Cancer Cells Using Aptamers Immobilized on a Microfluidic Channel," Anal. Chem., 81:1033-1039 (2009).

Zheng et al., "Aptamer-Functionalized Barcode Particles for the Capture and Detection of Multiple Types of Circulating Tumor Cells," Adv. Mater., 26:7333-7338 (2014).

Xu et al., "Aptamer-Based Microfluidic Device for Enrichment, Sorting, and Detection of Multiple Cancer Cells," Anal. Chem., 81:7436-7442 (2009).

Sheng et al., "Aptamer-Enabled Efficient Isolation of Cancer Cells from Whole Blood Using a Microfluidic Device," Anal. Chem., 84:4199-4206 (2012).

Shen et al., "Specific Capture and Release of Circulating Tumor Cells Using Aptamer-Modified Nanosubstrates," Adv. Mater., 25:2368-2373 (2013).

Chen et al., "Targeted isolation and analysis of single tumor cells with aptamer-encoded microwell array on microfluidic device," Lab Chip, 12:5180-5185 (2012).

Liu et al., "Rare cell chemiluminescence detection based on aptamer-specific capture in microfluidic channels," Biosensors and Bioelectronics, 28:438-442 (2011).

Lin et al., "Assay of multiplex proteins from cell metabolism based on tunable aptamer and microchip electrophoresis," Biosensors and Bioelectronics, 63:105-111 (2015).

Martin et al., "Capturing cancer cells using aptamer-immobilized square capillary channels," Mol. BioSyst., 7:1720-1727 (2011).

Cabodi et al., "Entropic Recoil Separation of Long DNA Molecules," Anal. Chem., 74:5169-5174 (2002).

Benitez et al., "Microfluidic Extraction, Stretching and Analysis of Human Chromosomal DNA from Single Cells," Lab Chip, 12(22):4848-4854 (Nov. 21, 2012).

Saad et al., "Epidermal growth factor receptor T790M mutation-positive metastatic non-small-cell lung cancer: focus on osimertinib (AZD9291)," OncoTargets and Therapy, 10:1757-1766 (2017).

International Searching Authority (KIPO) International Search Report and Written Opinion issued in counterpart PCT/US2012/041136, dated Jan. 2, 2013.

* cited by examiner

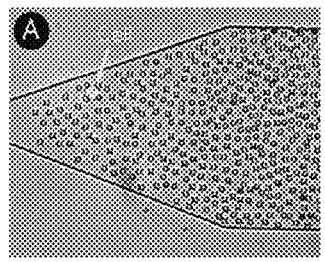 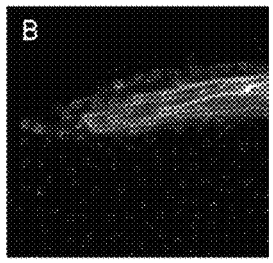 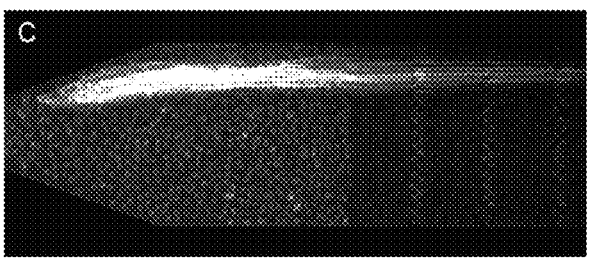
FIG. 11A  FIG. 11B  FIG. 11C
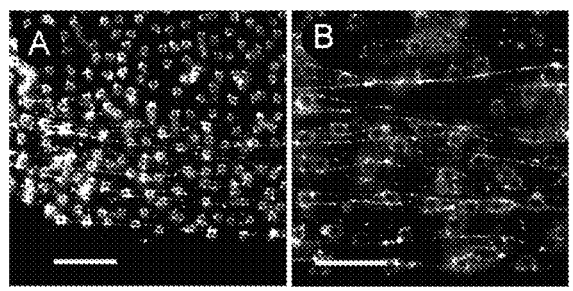
FIG. 12A  FIG. 12B
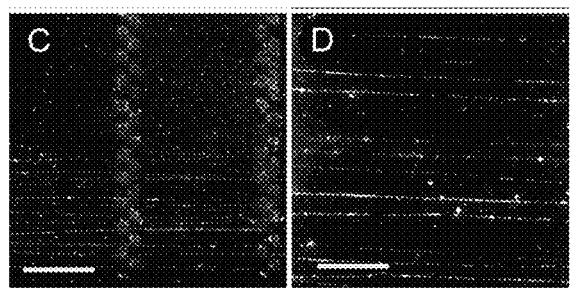
FIG. 12C  FIG. 12D

MICROFLUIDIC DEVICE FOR EXTRACTING, ISOLATING, AND ANALYZING DNA FROM CELLS

CROSS-REFERENCE TO RELATED APPLICATIONS

This application is a continuation of U.S. patent application Ser. No. 15/936,349, filed Mar. 26, 2018, which issued as U.S. Pat. No. 10,947,528 on Mar. 16, 2021, which is a continuation of U.S. patent application Ser. No. 14/124,479, filed Mar. 10, 2014, which issued as U.S. Pat. No. 9,926,552 on Mar. 27, 2018, which is a U.S. National Phase filing under 35 U.S.C. § 371 of International Application No. PCT/US2012/0041136, filed Jun. 6, 2012, and published as WO 2012/170560 on Dec. 13, 2012, which claims priority benefit of U.S. Provisional Patent Application Ser. No. 61/493,748, filed Jun. 6, 2011, and U.S. Provisional Patent Application Ser. No. 61/548,896, filed Oct. 19, 2011, the disclosures of which are hereby incorporated by reference herein in their entirety.

GOVERNMENT RIGHTS STATEMENT

This invention was made with Government support under grant number U54CA143876 awarded by the National Institutes of Health. The Government has certain rights in the invention.

FIELD OF THE INVENTION

The present invention relates to a microfluidic device for, inter alia, extracting, isolating, and analyzing DNA from a cell. The present invention also relates to systems that include the microfluidic device. The present invention further relates to methods of making and using the microfluidic device and related systems thereof.

BACKGROUND OF THE INVENTION

Genome-wide analysis of human DNA in small cell populations is becoming increasingly important in modern medicine in applications ranging from cancer to understanding tissue development. While there are many commercially available macroscale sample preparation kits and microfluidic devices for nucleic acid isolation, it remains extremely challenging to efficiently extract and purify DNA from a few cells, let alone a single cell. The traditional vial-based extraction techniques utilize electrostatic interactions of DNA with biochemically functionalized magnetic microparticles or spin columns that are used to separate nucleic acids from the rest of the cell lysate. An appreciable fraction of genomic DNA is always lost during the purification process, which presents a serious problem when the whole genome of small cell populations such as rare cancer cells or stem cells needs to be analyzed. Additional losses are introduced during sample manipulation when the purified DNA is eluted from the microparticles or spin columns. The utility of DNA extraction tools for medically relevant genome-wide studies would be enhanced by integrating these tools with single-molecule spectroscopy, imaging, and sorting systems (Refs. A1-A3).

The macroscale DNA extraction techniques have been recently investigated by various research groups (Refs. A4-A13) and implemented in microfluidic systems that provide handling and manipulation of small sample and reagent volumes in engineered microstructures. Microfluidic devices could perform the analysis automatically in an enclosed system which reduces the chance for human error and cross contamination. These devices may also reduce the time and the cost of the analysis by taking advantage of high reaction rates at the microscale and generally provide higher extraction efficiencies by utilizing features with high surface-to-volume ratios for improved DNA extraction, but they still rely on DNA adsorption to silica or other biochemically functionalized surfaces. The binding affinity is extremely sensitive to temperature, pH, and buffer composition which need to be optimized carefully to minimize DNA losses. Even after meticulous optimization it is difficult to ensure that all the DNA fragments get adsorbed and the whole genome is represented in purified extracts obtained from a few cells. Fundamentally different approaches to genomic DNA capture should therefore be explored to improve and facilitate the extraction efficiency.

There are a variety of commercially available DNA extraction kits that advertise the ability to extract DNA from a few cells. See e.g. Applied Biosystems® Arcturus® PicoPure® DNA. However, unlike microfluidic devices, these kits do not perform purification of the extracted DNA and simply focus on creating buffer chemistries that do not interfere with PCR amplification. Additionally, whole genome amplification has amplification induced errors and template biases that are a problem with such systems. There is a need for DNA purification systems for single-molecule fluorescence studies not provided in the art. There is also a need for systems that decrease the amplification induced errors for applications such as whole genome amplification.

The present invention is directed to overcoming these and other deficiencies in the art.

SUMMARY OF THE INVENTION

In one aspect, the present invention relates to a microfluidic device for extracting and isolating DNA from at least one cell. The device includes a support having an inlet port for receiving a sample containing the at least one cell, an outlet port for dispensing DNA isolated from the at least one cell, and a microfluidic channel disposed within the support and extending from the inlet port to the outlet port. The microfluidic channel includes a micropillar array, an inflow channel disposed between the inlet port and the micropillar array, and an outflow channel disposed between the micropillar array and the outlet port. The micropillar array includes micropillars spatially configured to entrap, by size exclusion, the at least one cell, to immobilize DNA released from the at least one cell, and to maintain the immobilized DNA in elongated or non-elongated form when hydrodynamic force is applied to the microfluidic channel.

In one embodiment, the microfluidic device of the present invention further includes a hydrodynamic flow controller in functional communication with the outlet port and effective to generate hydrodynamic flow of a fluid from the inlet port to the outlet port.

In another aspect, the present invention relates to a method of making the microfluidic device of the present invention. This method involves providing a support and forming within the support the inlet port for receiving a sample containing at least one cell, the outlet port for dispensing DNA isolated from the at least one cell, and the microfluidic channel disposed within the support and extending from the inlet port to the outlet port. In one embodiment, this method further involves providing a hydrodynamic flow controller in functional communication with the outlet port and effective to generate hydrodynamic flow of a fluid from the inlet port to the outlet port.

In a further aspect, the present invention relates to a method of extracting and isolating DNA from at least one cell. This method involves providing a microfluidic device of the present invention and flowing a sample that includes at least one cell through the microfluidic channel of the microfluidic device, thereby causing the DNA to be released from the at least one cell and immobilized within the micropillar array of the microfluidic device.

In one embodiment, this method of the present invention further involves analyzing the immobilized DNA while the DNA is maintained within the micropillar array.

In another embodiment, this method of the present invention further includes removing the immobilized DNA from the micropillar array to yield isolated DNA. This embodiment can further involve analyzing the isolated DNA.

In a further embodiment, this method of the present invention further involves, prior to the removing step, purifying the immobilized DNA to detach proteins or other biomaterials bound or in contact with the immobilized DNA or released from the cell.

In another aspect, the present invention relates to a microfluidic system for extracting, isolating, and analyzing DNA from at least one cell. The microfluidic system includes a microfluidic device of the present invention and an apparatus for analyzing DNA immobilized on the micropillar array of the microfluidic device.

In one embodiment, this microfluidic system further includes at least one reagent, where the reagent can include, without limitation, a cell lysis agent, a DNA labeling agent, a restriction enzyme, an anti-electrostatic microfluidic channel blocking agent, and the like.

In another aspect, the present invention relates to a microfluidic-nanofluidic system for extracting, isolating, and analyzing DNA from at least one cell. The microfluidic-nanofluidic system includes a microfluidic device of the present invention, a nanofluidic device in fluid communication with the outlet port of the microfluidic device so as to receive DNA released from the at least one cell, and an apparatus for analyzing single DNA molecules released from the at least one cell. The nanofluidic device of this system can function to isolate a single DNA molecule from the released DNA.

In another aspect, the present invention relates to a method of extracting, isolating, and analyzing a single DNA molecule from at least one cell by providing a microfluidic-nanofluidic system of the present invention and flowing a sample having at least one cell through the microfluidic channel of the microfluidic device of the system, thereby causing the DNA to be released from the at least one cell and temporarily immobilized within the micropillar array of the microfluidic device. This method also involves passing the DNA through the nanofluidic device to isolate a single DNA molecule from the released and de-immobilized DNA and using the apparatus to analyze the isolated single DNA molecule.

In one embodiment, this method further involves analyzing the immobilized DNA while the DNA is maintained within the micropillar array.

In another embodiment, this method further involves removing the immobilized DNA from the micropillar array to yield isolated DNA. This embodiment further involves analyzing the isolated DNA.

In a further embodiment, this method further involves, prior to the removing step, purifying the immobilized DNA to detach proteins or other biomaterials bound or in contact with the immobilized DNA.

The device, systems, and methods of the present invention provide numerous advantages over the existing art. For example, in one application, the present invention provides devices, systems, and methods for the extraction and the single-molecule analysis of human genomic DNA from small cell populations and individual single cells. In one embodiment, the present invention provides a polydimethylsiloxane (PDMS) microfluidic device for DNA extraction integrated with a nanofluidic device for single-molecule fluorescence analysis. The microfluidic device includes an array of micropillars in which cells can be immobilized and chemically lysed. The released long strands of genomic DNA can then become suspended in the same micropillar array by hydrodynamic forces while the rest of the cell lysate is washed away. Compared to the conventional methods, the extraction method of the present invention does not rely on DNA purification with magnetic microparticles or spin columns, thus allowing separation of genomic DNA from mitochondrial DNA and RNA. The isolated or purified genomic DNA can then be released from the micropillar array by enzymatic digestion. Thus, in one embodiment, the output of the microfluidic channel can be aligned with the input of the nanofluidic component through which the DNA fragments are driven electrophoretically and analyzed one molecule at a time by observing single-molecule fluorescence.

In certain applications and related embodiments of the present invention, the technique of extraction and isolation (also referred to as purification) of DNA by physical trapping in tapered arrays of micropillars by microfluidic flow is fundamentally different from the alternative approaches which rely on electrostatic interactions between DNA and the microchannel walls or biochemically functionalized microparticles. By way of contrast, in the present invention, long strands of genomic DNA released from the lysed cells become immobilized in the tapered array of micropillars (also referred to as microposts) by hydrodynamic flow due to their relatively large size while the rest of the cellular contents are washed away by pressure-driven flow. The flow rate can be optimized so that no DNA shearing occurs in the microchannel. Using the microfluidic device of the present invention, thorough removal of cellular debris can be accomplished, which is important for the subsequent single-molecule studies as the labeled fragment could interfere with the analysis.

The present invention further provides a method of separation by hydrodynamic forces that allows for the separation of genomic DNA not only from proteins and lipids which are primary components of the cell lysate, but also from other nucleic acids such as mitochondrial DNA and RNA. This cannot be achieved with the alternative extraction methods of the existing art.

The devices, systems, and methods of the present invention also provide for the immobilized DNA to be labeled under continuous flow and the unbound dye to be removed from the buffer, which facilitates single-molecule analysis in the nanochannels using fluorescent microscopy techniques by reducing background fluorescence.

Further, the present invention provides a means for the extracted DNA to flow from the microfluidic component directly into nanofluidic components so that the extracted DNA is never removed from the integrated micro/nanofluidic platform, which prevents inadvertent losses during sample manipulations. Therefore, the microfluidic device and related systems and methods of the present invention are thus suitable for genome-wide analysis of single cells.

In various embodiments, the microfluidic device of the present invention can be integrated with existing flow cytometry systems or microfluidic platforms and used in biomedical devices to extract, purify, and analyze DNA fragments in nanofluidic channels. The possible types of analysis enabled by the present invention include, without limitation, the monitoring of the distribution of mutation sites and epigenetic marks in rare cancer cells and/or stem cells in response to treatment or changes in the environment.

In one embodiment, the microfluidic portion of the device can be fabricated in various molded polymers using standard soft-lithography and mould-replica techniques. The nanofluidic portion, on the other hand, may be fabricated in UV fused silica to avoid autofluorescence.

In other embodiments, the microfluidic device of the present invention can be realized on other material platforms such as silicon, fused silica, glass, and others. Alternative versions of the invention could include an integrated polymerase chain reaction (PCR) chamber for on-chip genome amplification. The nanofluidic component of the device could contain bifurcated channels for DNA fragment sorting based on size or coincident fluorescent intensity.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIGS. 11A-11C: FIG. 11A: Single cell immobilized in a random array of micropillar obstacles. FIG. 11B: Detailed fluorescent image of DNA strands looped around the micropillars and suspended by hydrodynamic flow. FIG. 11C: Elongated DNA strands from the cells shown in FIG. 11A. The multiply folded strands extend ~27 mm into the microchannel.

FIGS. 12A-12D: Human chromosomes 17 selectively labelled with whole chromosome paints. FIG. 12A: Unwrapped chromosomes looped around randomly spaced micropillars. FIG. 12B: Detailed fluorescent image of hybridized DNA strands. FIG. 12C: Elongated DNA strands suspended between arrays of micropillars. FIG. 12D: Detailed image of the elongated strands. The scale bars are 20, 10, 50, and 20 μm, respectively.

FIG. 13A: Bright field image of 70 cells captured in a micropillar obstacle array. FIG. 13B: Fluorescent image of the released DNA. FIG. 13C: Sequence of fluorescent images showing digestion of chromosomal DNA extracted from the cells shown in FIG. 13A. FIG. 13D: Amounts of DNA collected from different number of M0-91 cells in the microfluidic device. The total elution volume for each sample was 20 μL. The solid line corresponds to the expected mass assuming 6.6 pg/cell genomic DNA content.

DETAILED DESCRIPTION OF THE INVENTION

Figure 1:
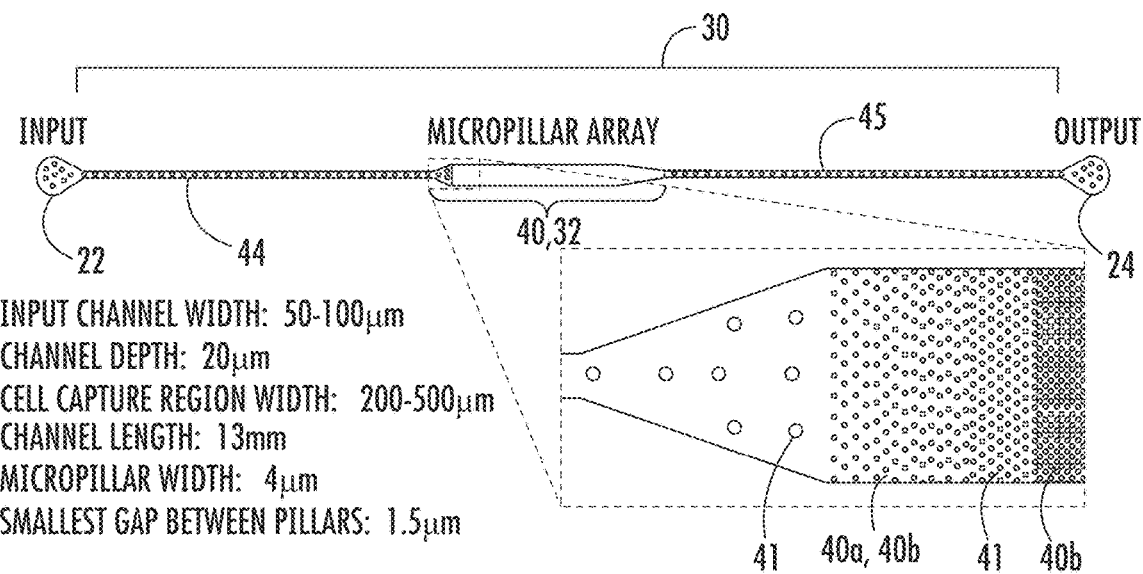
FIG. 1: Schematic representation of aspects of one embodiment of a microfluidic device of the present invention. While dimensions of the device are shown, the present invention is not limited to these dimensions.

The present invention generally relates to devices, systems, and methods that enable the extraction, isolation, and analyses of DNA from at least one cell. The present invention enables numerous applications that involve the production and use of a microfluidic device that is effective to trap single cells or a plurality of cells using size exclusion, and then extract DNA from the single cells or plurality of cells using hydrodynamic force. The microfluidic device and related systems are effective to immobilize the extracted DNA (i.e., DNA extracted from the cells) within a micropillar array under conditions sufficient to allow the DNA to become isolated from the cell, elongated, and maintained in an elongated form. While the DNA is maintained within the micropillar array, the present invention provides for the analysis of the DNA using standard DNA analysis techniques and protocols. Further, the microfluidic device of the present invention can be combined with a nanofluidic device to enable, inter alia, the isolation and analysis of a single DNA molecule from the isolated DNA.

The microfluidic devices, systems, and methods of the present invention are suitable for extracting, isolating, and analyzing DNA from any organism, whether the organism is prokaryotic or eukaryotic, including, without limitation, such organisms as bacteria, fungi, animals (including humans and any organism in the animal kingdom), plants, algae, marine organisms, etc. In addition, the microfluidic devices, systems, and methods of the present invention are suitable for extracting, isolating, and analyzing DNA from any type of cell of any of these organisms, including, without limitation, such types of cells as stem cells, cancer cells, leucocytes, etc. Further, the microfluidic devices, systems, and methods of the present invention can be used to extract and isolate DNA from a sample that contains only a single cell or a population of cells, whether the number of cells in the population is small (e.g., not more than 10 cells), medium, or large. The microfluidic devices, systems, and methods of the present invention can also be used to extract and isolate any type of DNA from the at least one cell, including, without limitation, genomic DNA (e.g., in the form of chromosomes) as well as any other type of DNA, including single molecules of DNA.

In one aspect, the present invention relates to a microfluidic device for, inter alia, extraction and the single-molecule analysis of human genomic DNA from small cell populations and individual single cells.

In another aspect, the present invention relates to a method for extraction and the single-molecule analysis of, inter alia, human genomic DNA from small cell populations and individual single cells.

As set forth herein, in one aspect, the present invention relates to a microfluidic device for extracting and isolating DNA from at least one cell. The device includes a support having an inlet port for receiving a sample containing the at least one cell, an outlet port for dispensing DNA isolated from the at least one cell, and a microfluidic channel disposed within the support and extending from the inlet port to the outlet port. The microfluidic channel includes a micropillar array, an inflow channel disposed between the inlet port and the micropillar array, and an outflow channel disposed between the micropillar array and the outlet port. The micropillar array includes micropillars spatially configured to entrap, by size exclusion, the at least one cell, to immobilize DNA released from the at least one cell, and to maintain the immobilized DNA in elongated or non-elongated form when hydrodynamic force is applied to the microfluidic channel. In one embodiment, the microfluidic device of the present invention further includes a hydrodynamic flow controller in functional communication with the outlet port and effective to generate hydrodynamic flow of a fluid from the inlet port to the outlet port. As discussed herein above, the microfluidic device of the present invention is suitable for extracting and isolating any type of DNA from any type of cell from any organism as set forth herein, whether the sample of DNA includes only a single cell or includes a population of cells.

FIGS. 1-7, 9-13, and 15 provide schematic, photographic, and photomicrographic views of illustrative embodiments and aspects of the microfluidic device of the present invention, as well as systems that include the microfluidic device of the present invention. While the aforementioned figures relate to and are further described in the examples provided herein below, certain of these figures are helpful in describing the microfluidic device and related systems in general terms.

FIG. 1 is a schematic illustration of one embodiment of aspects of a microfluidic device of the present invention. In particular, FIG. 1 illustrates inlet port 22, outlet port 24, and microfluidic channel 30, which are contained in a support portion of a microfluidic device of the present invention. While FIG. 1 includes particular dimensions of the microfluidic device shown in the schematic, the present invention is not limited to these dimensions. The dimensions of the inlet port, outlet port, microfluidic channel, micropillars, and micropillar array can be configured using any dimensions that are suitable for the functioning of the present invention as described herein.

Referring again to FIG. 1, in one embodiment, the microfluidic device of the present invention includes a support having inlet port 22 for receiving a sample containing at least one cell, outlet port 24 for dispensing DNA isolated from the at least one cell, and microfluidic channel 30 disposed within the support and extending from inlet port 22 to outlet port 24. Microfluidic channel 30 includes micropillar array 40, inflow channel 44 disposed between inlet port 22 and micropillar array 40, and outflow channel 45 disposed between micropillar array 40 and outlet port 24.

As shown in FIG. 1, in one embodiment, micropillar array 40 can form chamber 32. While FIG. 1 shows chamber 32 having a maximum width that is greater than the maximum width of inflow channel 44 and outflow channel 45, the present invention contemplates that chamber 32 or portions of chamber 32 can also have a maximum width that is less than or equivalent to the maximum width of each of inflow channel 44 and/or outflow channel 45. In FIG. 1, the beginning end and terminal end of chamber 32 (also shown as micropillar array 40) are substantially equivalent in width to both inflow channel 44 and outflow channel 45. As shown in the embodiment of FIG. 1, as chamber 32 progresses from its beginning end (which is connected to inflow channel 44), it gradually widens until it reaches its maximum width. At the terminal end of chamber 32, as shown in the embodiment of FIG. 1, chamber 32 gradually narrows or tapers until it has substantially the same width as outflow channel 45.

Again, the present invention is not limited to this particular geometry, but instead the present invention contemplates a chamber and microfluidic channel that is the same width, greater width, smaller width, or variable width (smaller, greater, and/or the same width) as the inflow channel and/or outflow channel. Further, the present invention contemplates that the inflow channel and the outflow channel can be of the same, substantially the same, or different widths and heights.

Figure 2:
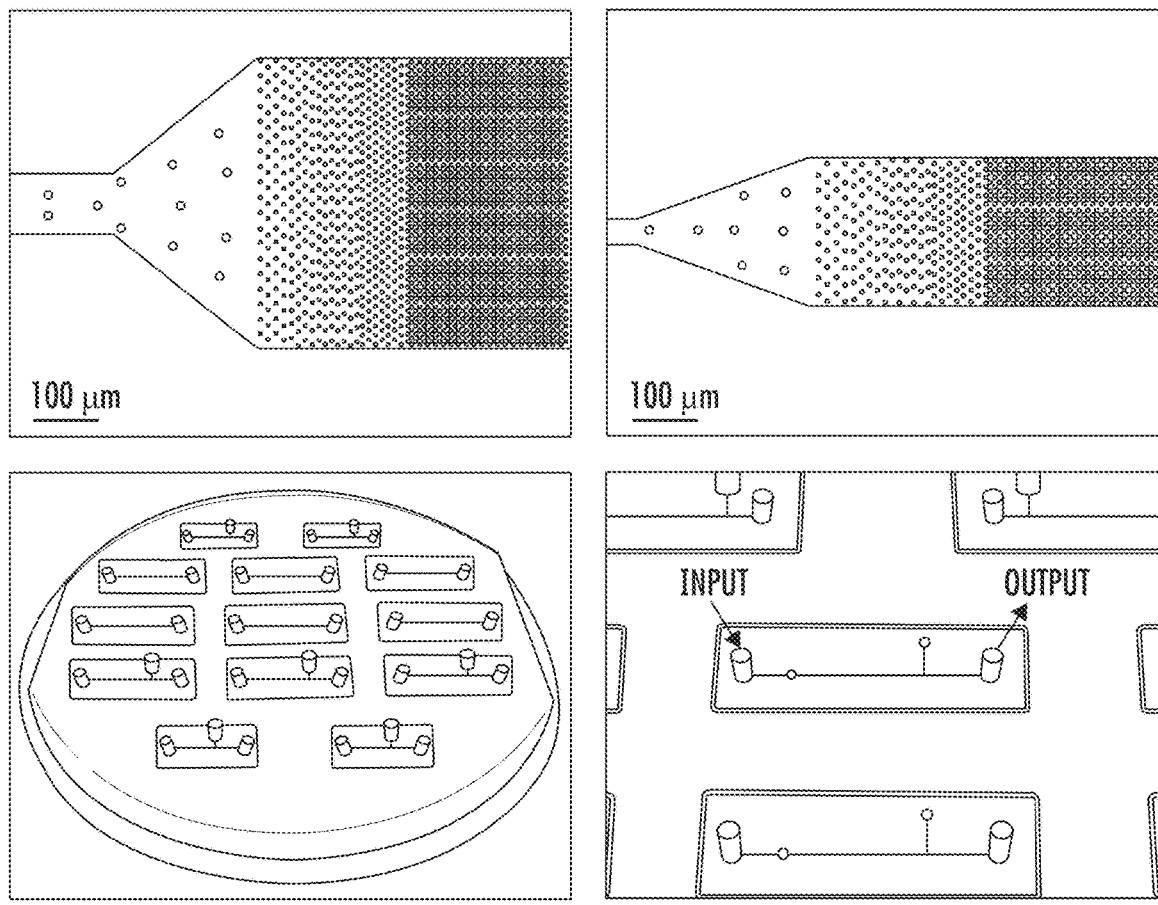
FIG. 2: Photomicrographs and photographs of views of various aspects of embodiments of a microfluidic device of the present invention. Photomicrographs are shown of the microarray of a microfluidic device of the present invention (top row). Photographs are shown of a number of fabricated PDMS microfluidic devices of the present invention (bottom row).

FIG. 2 provides several views of photomicrographs and photographs of aspects of a microfluidic device of the present invention. In particular, FIG. 2 (top row) includes photomicrographs of a micropillar array of a microfluidic device of the present invention. In the embodiment shown in FIG. 2, the micropillar array begins with relatively widely spaced micropillars, then provides more narrowly spaced micropillars of a smaller diameter, and then includes even more narrowly spaced (more densely spaced) micropillars. Again, the present invention is not limited to this particular configuration, which is only being presented for general illustrative purposes. FIG. 2 (bottom row) also includes photographs of a number of fabricated PDMS microfluidic devices of the present invention, showing their input and output ports, microfluidic channels, and supports.

Figure 3:
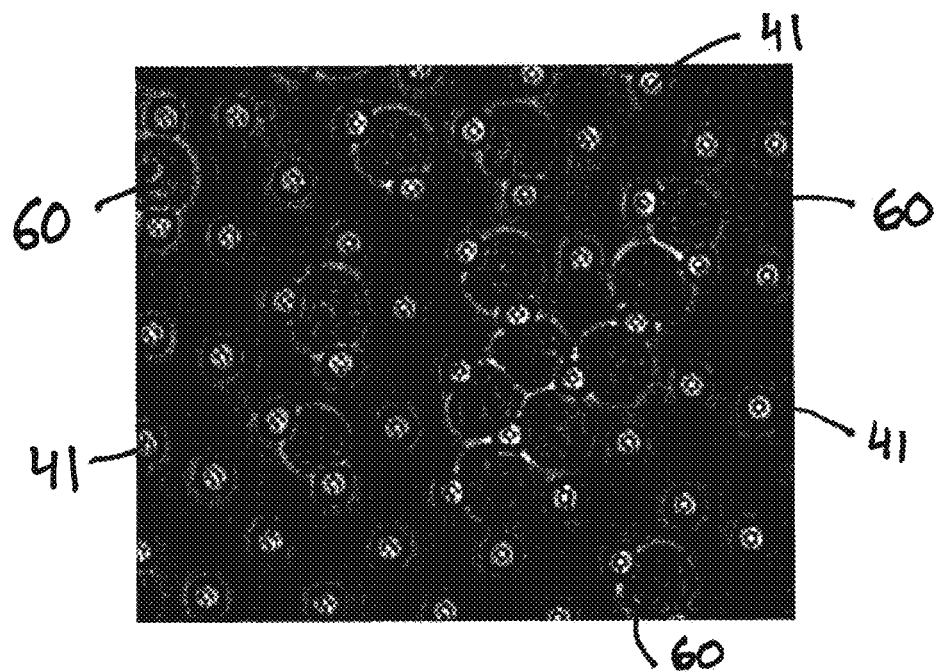
FIG. 3: Photomicrograph of hematopoietic stem-cells immobilized in a tapered micropillar array of one embodiment of a microfluidic device of the present invention.

FIGS. 3-6, 11-13, and 15 are photomicrographs that show cells and extracted DNA from cells as contained in a microfluidic device of the present invention. FIG. 3 provides a close view of multiple cells 60 (particularly hematopoietic stem-cells) immobilized by micropillars 41 of the micropillar array of one embodiment of a microfluidic device of the present invention. FIGS. 4-6, 11-13, and 15 include photomicrographs that show cells entrapped by the micropillars (by size exclusion), as well as the DNA extracted or being extracted from the entrapped cells, including DNA that is elongated within the micropillar array of the microfluidic device of the present invention.

As shown herein, the micropillar array includes micropillars that are spatially configured to entrap, by size exclusion, at least one cell, to immobilize DNA released from the at least one cell, and to maintain immobilized DNA in elongated form or non-elongated form when hydrodynamic force is applied to the microfluidic channel.

Figure 9:
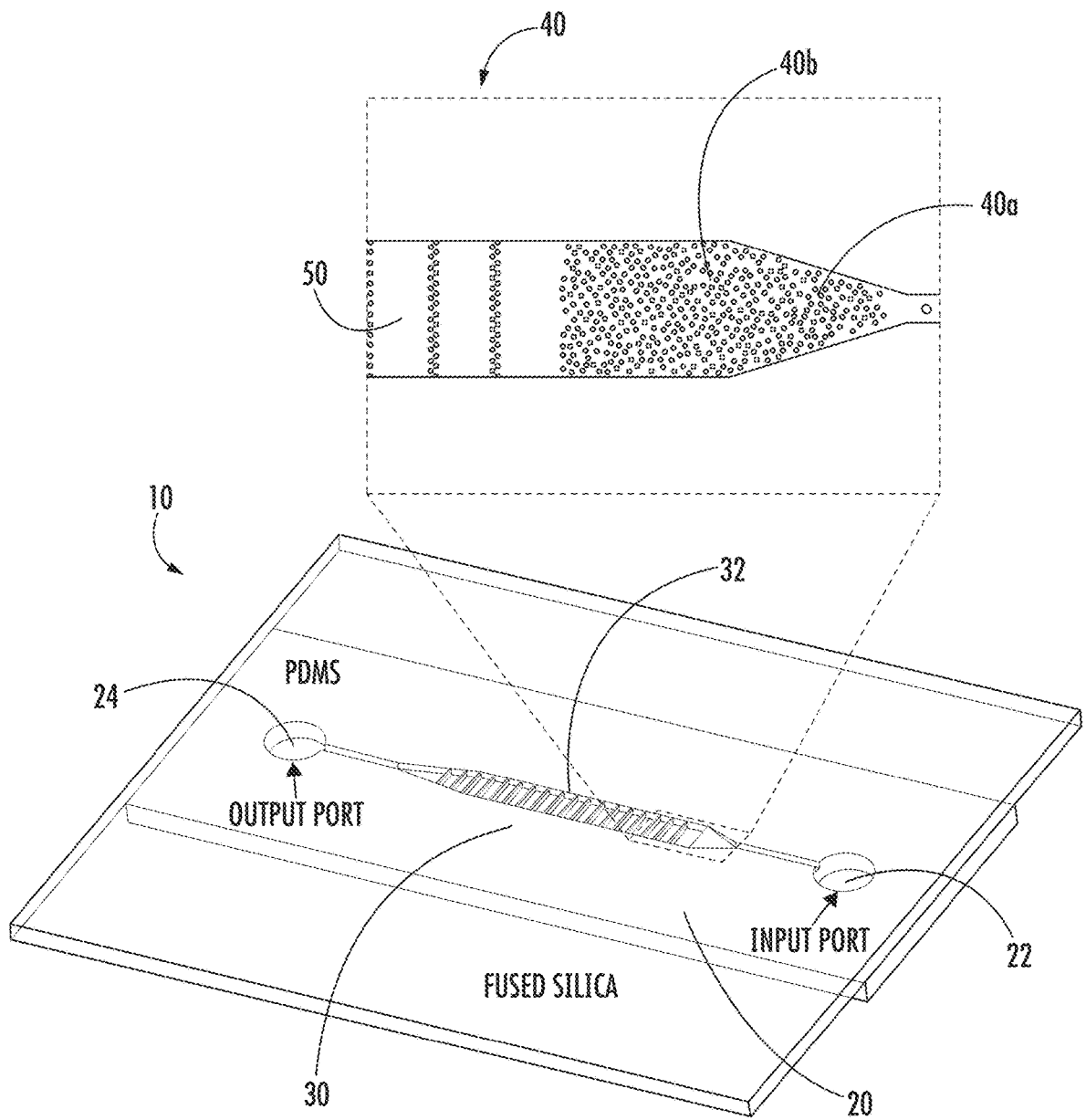
FIG. 9: Microfluidic device schematic (bottom portion) and a photomicrograph (top portion) of the channel with the random array of micropillar obstacles for cell capture and DNA extraction. The scale bar is 100 μm.

As shown in FIG. 9, in one embodiment, micropillar array 40 can include first region 40a having micropillars effectively spaced to entrap at least one cell; and second region 40b having micropillars effectively spaced to immobilize the released DNA and maintain the immobilized DNA in elongated form or non-elongated form. In a particular embodiment, the micropillars of second region 40b can be more closely spaced than the micropillars of first region 40a, though they need not be so configured.

The chamber of the microfluidic device of the present invention can be of any suitable length in accordance with the present invention. In one embodiment, the chamber can have a length sufficient to contain elongated chromosomal DNA released from the at least one cell. For example, in certain applications (e.g., studying human chromosomal DNA) the chamber can be configured to have a length sufficient to accommodate the longest human chromosome (e.g., approximately 8.5 cm in length). However, the present invention also contemplates chambers that are smaller in length, and even longer in length than the longest human chromosome when in elongated form.

As shown in FIG. 9, in a particular embodiment, chamber 32 can further include at least one linear array 50 of micropillars substantially spanning the width of chamber 32, thereby providing support for an immobilized and elongated DNA suspended within chamber 32. However, the micropillars need not span the width of the chamber.

Turning again to FIG. 1, as shown in that embodiment, inflow channel 44, outflow channel 45, or both inflow channel 44 and outflow channel 45 can have at least one micropillar 41 disposed therein. The micropillars provided in the inflow and outflow channels need not be included in order for the microfluidic device to function as described herein. However, in certain configurations, the micropillars are included to provide structural support. For example, without intending to be limiting of the present invention, micropillars can be included in the inflow channel and outflow channel to prevent collapse of the ceiling of the microfluidic channel when the device is operated under negative pressure (e.g., in syringe pull mode), even though the micropillars do not play any functional role in the extraction process. In certain configurations, if the inflow and outflow channels are sufficiently narrow, the device need not include any micropillars in the inflow or outflow channels for structural support purposes. Further, the micropillars contained in the micropillar array or in the inflow or outflow channels can be spaced in a random manner, a uniform manner, and/or in a desired spacing pattern. In addition, by varying the dimensions of the microfluidic channel and the micropillars, the device can be customized for a given type of cell.

As shown in FIG. 9 (bottom portion), support 20 can be made of various materials, including, without limitation, such materials as polydimethylsiloxane (PDMS), polystyrene, epoxy, polymethylmethacrylate (PMMA), and silica. In one embodiment, support 20 can be made of a material such as PDMS and then mounted onto another supportive structure, such as one made of fused silica, as shown in FIG. 9.

In one embodiment, the micropillar array can include micropillars that are coated with at least one binding agent that has affinity to at least a portion of the surface of the at least one cell. In a particular embodiment, the at least one binding agent can be, without limitation, an antibody, an aptamer, or the like. Other binding agents known in the art that are effective to attract cells are also contemplated by the present invention.

In one embodiment, the microfluidic device of the present invention can further include a hydrodynamic flow controller in functional communication with the outlet port and effective to generate hydrodynamic flow of a fluid from the inlet port to the outlet port. Suitable devices for use as a hydrodynamic flow controller of the present invention are known in the art and are contemplated for use in the present invention.

The present invention also relates to a method of making a microfluidic device for extracting and isolating DNA from at least one cell. The microfluidic device made by this method can also be used for analyzing the DNA that is extracted and isolated from the at least one cell.

The various components, materials, and techniques described herein above and below with respect to the microfluidic device of the present invention maintain their meaning in the context of this method of making the microfluidic device.

This method of making the microfluidic device involves providing a support and forming within the support an inlet port for receiving a sample containing at least one cell, an outlet port for dispensing DNA isolated from the at least one cell, and a microfluidic channel disposed within the support and extending from the inlet port to the outlet port. In one embodiment, this method further involves providing a hydrodynamic flow controller in functional communication with the outlet port, with the hydrodynamic flow controller being effective to generate hydrodynamic flow of a fluid from the inlet port to the outlet port.

As provided herein above, the support can be made of a material including, but not limited to, polydimethylsiloxane (PDMS), polystyrene, epoxy, polymethylmethacrylate (PMMA), and silica. In one embodiment, the step of forming the support can involve using standard soft-lithography and/or mold-replica techniques. In another embodiment, the step of forming the support can involve standard direct lithography and/or injection molding.

This method contemplates forming the various components and aspects of the microfluidic device as described herein above, including, without limitation, the support, inlet port, outlet port, microfluidic channel, chamber, micropillar array, first region of the micropillar array, second region of the micropillar array, micropillars making up the micropillar array, coated micropillars, the inflow channel, the outflow channel, the linear array, various patterns of the micropillar array (e.g., random patterns, uniformed patterns, desired spacing patterns such as custom designed patterns), etc. In view of the disclosure and knowledge available in the relevant art, one of ordinary skill in the art would readily understand how to make the microfluidic device of the present invention based on the description of these various components and aspects of the microfluidic device described herein. Therefore, such components and aspects are not reiterated herein with respect to the method of making the device, as the ordinarily skilled artisan has sufficient disclosure provided herein to make the microfluidic device according to the described method.

The present invention also relates to a method of extracting and isolating DNA from at least one cell. This method involves providing a microfluidic device of the present invention and flowing a sample that includes at least one cell through the microfluidic channel of the microfluidic device, thereby causing the DNA to be released from the at least one cell and immobilized within the micropillar array of the microfluidic device.

The various components, materials, and techniques described herein above and below with respect to the microfluidic device of the present invention maintain their meaning in the context of this method of using the microfluidic device to extract and isolate DNA from at least one cell.

As discussed herein above, this method is suitable for extracting and isolating DNA from any type of DNA from any type of cell from any organism as set forth herein, whether the sample of DNA includes only a single cell or includes a population of cells. Further, the devices, systems, and methods of the present invention can be used to compare DNA from different cells or types of cells simultaneously.

In one embodiment, the flowing step of this method involves applying sufficient hydrodynamic flow to elongate the immobilized DNA within the micropillar array.

In a particular embodiment, the flowing step of this method involves (i) introducing the sample into the inlet port of the microfluidic device under sufficient hydrodynamic flow to entrap, by size exclusion, the at least one cell within the micropillar array; and (ii) lysing the entrapped cell under sufficient hydrodynamic flow to release DNA contained in the cell, thereby causing the released DNA to be immobilized within the micropillar array of the microfluidic device.

In one embodiment, this method of the present invention further involves analyzing the immobilized DNA while the DNA is maintained within the micropillar array. This embodiment can further involve analyzing the isolated DNA. With respect to this analyzing step, the present invention contemplates the use of any technique and related tools used in the art to analyze such immobilized DNA, including, without limitation, methods and tools involving fluorescence microscopy, optical microscopy, hybridization assays, and the like.

In another embodiment, this method of the present invention further includes removing the immobilized DNA from the micropillar array to yield isolated DNA. The removing step can involve subjecting the immobilized DNA to hydrodynamic force sufficient to pass the DNA through the micropillar array and into the outflow channel of the microfluidic device of the present invention. In another embodiment, the removing step can involve subjecting the immobilized DNA to enzymatic digestion sufficient to fragment the DNA so that it passes through the micropillar array and into the outflow channel. Suitable enzymes and any related buffers for use in this enzymatic digestion are well known in the art, and are contemplated by the present invention. In another embodiment, the removing step can involve, without limitation, sonicating the microfluidic device and subjecting the immobilized DNA to hydrodynamic force sufficient to pass the DNA through the micropillar array and into the outflow channel of the microfluidic device.

In a particular embodiment, after removing the immobilized DNA from the micropillar array of the microfluidic device to yield isolated DNA, the isolated DNA can be analyzed. With respect to this analyzing step, the present invention contemplates the use of any technique and related tools used in the art to analyze such isolated DNA, including, without limitation, techniques and tools involving nucleic acid amplification, absorbance, fluorospectrometry, spectrophotometry, gel electrophoresis, nanofluidics, protein assays, microarrays, qPCR, fluorescence microscopy, optical microscopy, hybridization assays, and the like.

In a further embodiment, this method of the present invention further involves, prior to the removing step, purifying the immobilized DNA to detach proteins or other biomaterials bound or in contact with the immobilized DNA or released from the cell. In a particular embodiment, the purifying step can include contacting a proteinase buffer to the immobilized DNA. Suitable proteinase buffers and related techniques and protocols are well known in the art for this purpose, and are contemplated by the present invention.

The present invention relates to a microfluidic system for extracting, isolating, and analyzing DNA from at least one cell. The microfluidic system includes a microfluidic device of the present invention and an apparatus for analyzing DNA immobilized on the micropillar array of the microfluidic device.

The various components, materials, and techniques described herein above and below with respect to the microfluidic device of the present invention maintain their meaning in the context of this microfluidic system for extracting, isolating, and analyzing the DNA from the at least one cell.

In one embodiment, this microfluidic system further includes at least one reagent, where the reagent can include, without limitation, a cell lysis agent, a DNA labeling agent, a restriction enzyme, an anti-electrostatic microfluidic channel blocking agent, and the like. As used with the present invention, DNA labeling can be used to indicate the presence of a specific gene, mutation, or epigenetic modification of the DNA.

The apparatus of the microfluidic system of the present invention can include any apparatus useful for analyzing DNA immobilized on the micropillar array of the microfluidic device of the present invention. Such apparatuses are known in the art and are contemplated by the present invention. In particular embodiments, the apparatus of the microfluidic system can include, without limitation, an apparatus such as a microscope, fluorescent microscope, hybridization array, mass spectrometer, DNA sequencer, syringe pump, valve system, inverted microscope, syringe, microfluidic tubing, and the like.

In a further embodiment, the microfluidic system of the present invention can further include at least one reagent. Suitable reagents can include, without limitation, a cell lysis agent, a DNA labeling agent, a restriction enzyme, an anti-electrostatic microfluidic channel blocking agent, and the like.

The present invention further relates to a microfluidic-nanofluidic system for extracting, isolating, and analyzing DNA from at least one cell. The microfluidic-nanofluidic system includes a microfluidic device of the present invention, a nanofluidic device in fluid communication with the outlet port of the microfluidic device so as to receive DNA released from the at least one cell, and an apparatus for analyzing single DNA molecules released from the at least one cell. The nanofluidic device of this system functions to isolate a single DNA molecule from the released DNA.

The various components, materials, and techniques described herein above and below with respect to the microfluidic device of the present invention maintain their meaning in the context of this microfluidic-nanofluidic system for extracting, isolating, and analyzing the DNA from the at least one cell.

Figure 7:
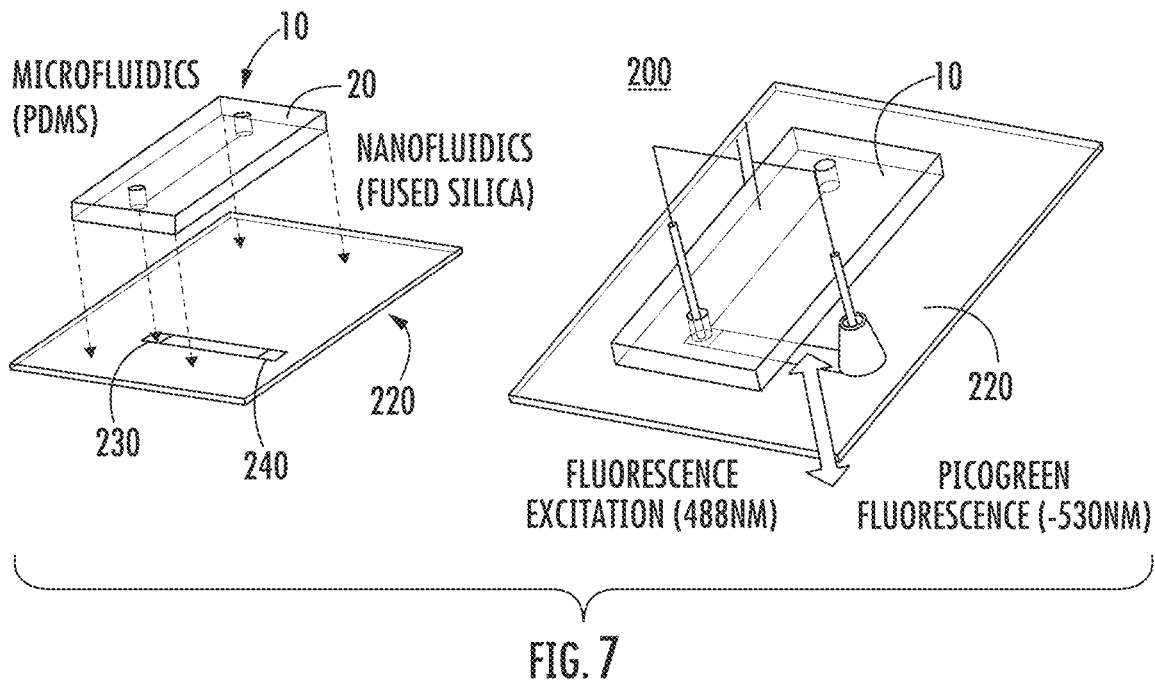
FIG. 7: Schematic of one embodiment of a microfluidic-nanofluidic system of the present invention for use in DNA extraction and single-molecule analysis. The microfluidic device and nanofluidic device are shown prior to integration (left portion) and after integration (right portion).

In one embodiment, the microfluidic-nanofluidic system is configured so that the microfluidic device is mounted on the nanofluidic device, and so that the outlet port of the microfluidic device is connected to an inlet port of the nanofluidic device. FIG. 7 illustrates one particular embodiment of a microfluidic-nanofluidic system according to the present invention.

The nanofluidic device of the microfluidic-nanofluidic system can be formed from any material suitable for making a nanofluidic device as described herein for use along with the microfluidic device of the present invention, as described herein. In one embodiment, the nanofluidic device of the microfluidic-nanofluidic system is formed from a material such as, but not limited to, fused silica, silicon, glass, quartz, polydimethylsiloxane (PDMS), polymers, and the like.

The nanofluidic device of the microfluidic-nanofluidic system can be configured to isolate the single DNA molecule under pressure driven flow and/or electrically driven flow. Suitable nanofluidic devices that operate under pressure driven flow and/or electrically driven flow are known in the art, and are contemplated by the present invention.

FIG. 7 is a schematic of one embodiment of a microfluidic-nanofluidic system of the present invention for use in DNA extraction and single-molecule analysis. As shown in FIG. 7, microfluidic-nanofluidic system 200 includes microfluidic device 10 and nanofluidic device 220. In the embodiment shown in FIG. 7, support 20 of microfluidic device 10 can be made of PDMS and mounted to nanofluidic device 220, so that the outlet port of microfluidic device 10 empties into inlet port 230 of nanofluidic device 220, which as shown can be made of fused silica. FIG. 7 shows microfluidic device 10 and nanofluidic device 220 prior to integration/mounting (left portion of FIG. 7) and after integration/mounting (right portion of FIG. 7).

The present invention also relates to a method of extracting, isolating, and analyzing a single DNA molecule from at least one cell by providing a microfluidic-nanofluidic system of the present invention and flowing a sample having at least one cell through the microfluidic channel of the microfluidic device of the system, thereby causing the DNA to be released from the at least one cell and temporarily immobilized within the micropillar array of the microfluidic device. This method also involves passing the DNA through the nanofluidic device to isolate a single DNA molecule from the released and de-immobilized DNA and using the apparatus to analyze the isolated single DNA molecule.

Similar to the method of using the microfluidic system of the present invention, as described herein above, this method of using the microfluidic-nanofluidic system is suitable for extracting, isolating, and analyzing any type of DNA from any type of cell from any organism as set forth herein, whether the sample of DNA includes only a single cell or includes a population of cells.

The various components, materials, and techniques described herein above and below with respect to the microfluidic device, microfluidic system, and microfluidic-nanofluidic system of the present invention maintain their meaning in the context of this method of using the microfluidic-nanofluidic system for extracting, isolating, and analyzing a single DNA molecule from the at least one cell.

In one embodiment, the flowing step involves applying sufficient hydrodynamic flow to elongate the immobilized DNA within the micropillar array. The parameters can be determined by one of ordinary skill in the art, depending on the known dimensions of the microfluidic device of the present invention. Without intending to limit the scope of the present invention, in one particular embodiment, a suitable flow can range from about 10-100 nL/minute for a device or system of the present invention having typical channel dimensions as set forth herein. In view of the disclosure provided herein and the knowledge in the relevant art, one of ordinary skill in the art would be able to determine suitable hydrodynamic flow rates for use in the devices, systems, and methods of the present invention.

In another embodiment, the flowing step involves: (i) introducing the sample into the inlet port of the microfluidic device under sufficient hydrodynamic flow to entrap, by size exclusion, the at least one cell within the micropillar array of the microfluidic device; and (ii) lysing the entrapped cell under sufficient hydrodynamic flow to release DNA contained in the cell, thereby causing the released DNA to be immobilized within the micropillar array of the microfluidic device.

In one embodiment, this method further involves analyzing the immobilized DNA while the DNA is maintained within the micropillar array. As set forth herein, any technique or tool used in the art to analyze such immobilized DNA can be used herein. In a particular embodiment, the analyzing step involves conducting techniques that include, without limitation, nucleic acid amplification, absorbance, fluorospectrometry, spectrophotometry, gel electrophoresis, nanofluidics, protein assays, microarrays, qPCR, fluorescence microscopy, optical microscopy, hybridization assays, and the like.

In another embodiment, this method further involves removing the immobilized DNA from the micropillar array to yield isolated DNA. In a particular embodiment, the removing step involves subjecting the immobilized DNA to hydrodynamic force sufficient to pass the DNA through the micropillar array and into the outflow channel of the microfluidic device.

In another embodiment, the removing step involves subjecting the immobilized DNA to enzymatic digestion sufficient to fragment the DNA so that it passes through the micropillar array and into the outflow channel. Suitable buffers, enzymes, and other aspects for such enzymatic digestion are provided herein, and are known in the art, and contemplated by the present invention.

In another embodiment, this method further involves removing the immobilized DNA from the micropillar array to yield isolated DNA. This embodiment further involves analyzing the isolated DNA using techniques known in the art, including, for example, those described elsewhere herein, such as, but not limited to, nucleic acid amplification, absorbance, fluorospectrometry, spectrophotometry, gel electrophoresis, nanofluidics, protein assays, microarrays, qPCR, fluorescence microscopy, optical microscopy, hybridization assays, and the like.

In a further embodiment, this method further involves, prior to the removing step, purifying the immobilized DNA to detach proteins or other biomaterials bound or in contact with the immobilized DNA or released from the cell. In a particular embodiment, the purifying step can include contacting a proteinase buffer to the immobilized DNA. Suitable proteinase buffers and related techniques and protocols are well known in the art for this purpose, and are contemplated by the present invention.

Figure 10:
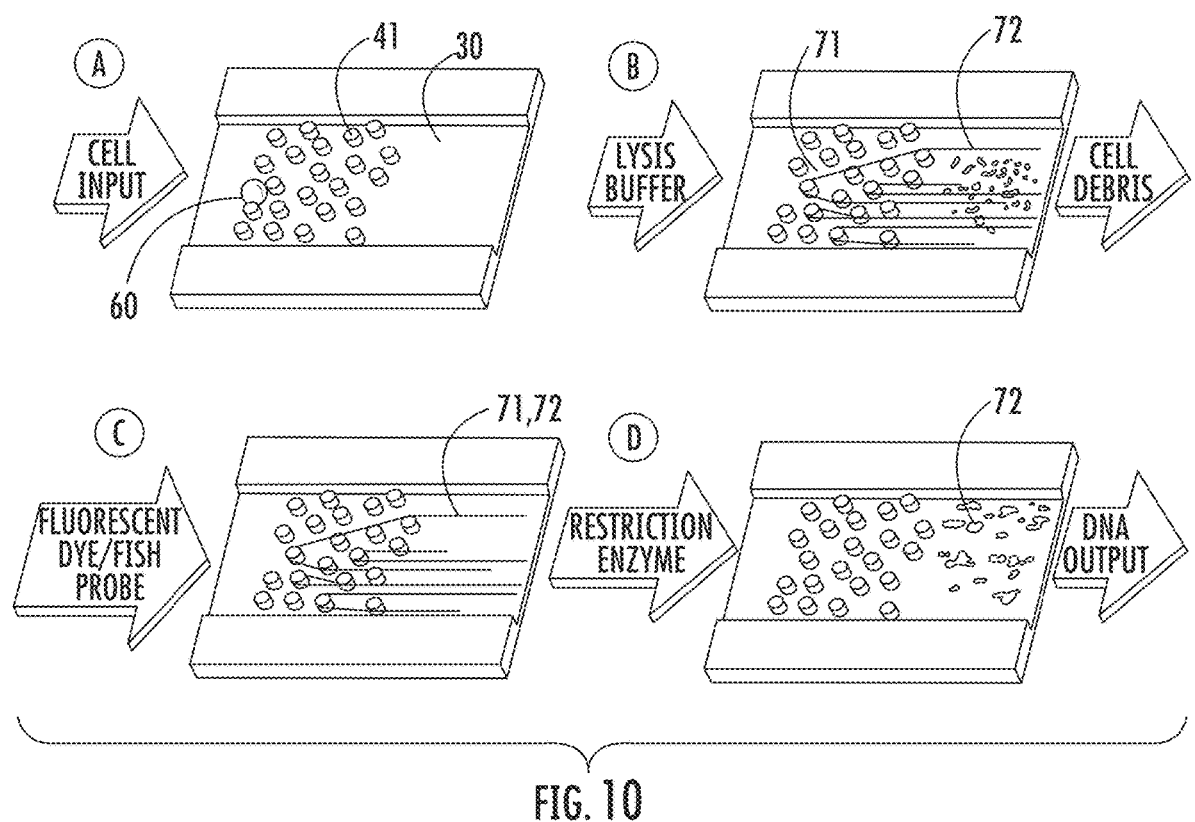
FIG. 10: Schematic representation of aspects of one embodiment of a microfluidic device of the present invention in operation: First Step A (Top Left Step): Single cell is captured in the random array of micropillars by size exclusion. Second Step B (Top Right Step): The cell is lysed with a surfactant that removes the cell debris and strips off proteins from genomic DNA, leaving it suspended in micropillar array. Third Step C (Bottom Left Step): The DNA is intercalated or hybridized with FISH probes. Fourth Step D (Bottom Right Step): The DNA is released from the array by enzymatic digestion with restriction endonucleases.

FIG. 10 illustrates various aspects of one embodiment of how a microfluidic device of the present invention can be used to extract, isolate, and analyze DNA from a cell. Briefly, as shown in First Step A of FIG. 10, in one embodiment, single cell 60 is captured in a random micropillar array contained in microfluidic channel 30, where cell 60 is entrapped by micropillars 41 by size exclusion. Cell 60 flows into microfluidic channel 30 from the inlet port of the support of the microfluidic device. Cell 60 can then be disrupted using hydrodynamic force in order to allow DNA to escape from cell 60. As shown in Second Step B of FIG. 10, in one embodiment, a lysis buffer (e.g., surfactant) can be added via the inlet port in order to remove the cell debris and strip off proteins from immobilized DNA 71 (e.g., genomic DNA), leaving the DNA suspended in the micropillar array, with some of the DNA being in the form of elongated DNA 72. The cell debris can be washed out of the microfluidic device through the outlet port of the device. As shown in Third Step C of FIG. 10, immobilized DNA 71 (including elongated DNA 72 as well as non-elongated DNA) can then be intercalated or hybridized with probes (e.g., fluorescent dye/FISH probes) in order to stain the DNA for visualization/analysis. As shown in Fourth Step D of FIG. 10, the DNA can then be released from the micropillar array by enzymatic digestion (e.g., with restriction endonucleases), which can be done by adding enzymes (e.g., restriction enzymes) through the inlet port of the microfluidic device. Fourth Step D of FIG. 10 shows fragmented DNA 75 (i.e., digested DNA) moving off of the micropillars and toward the outlet port of the microfluidic device, where the DNA can be collected and/or sent to a nanofluidic device or other DNA analysis tool or machine for further analysis.

In order to provide an overview of aspects of the present invention, provided below is a discussion of the embodiments of FIGS. 1-8. In one embodiment of the present invention, the microfluidic portion of the device shown schematically in FIG. 1 (images of fabricated devices are presented in FIG. 2) was fabricated in polydimethylsiloxane (PDMS) using standard soft-lithography and mould-replica techniques. The nanofluidic device portion was fabricated in fused silica using standard optical lithography. Suitable nanofluidic devices and related methods of using the nanofluidic devices for use in the present invention are described in WO 2011/017677 to Craighead et al. and WO 2011/017681 to Craighead et al., the disclosures of which are hereby incorporated by reference herein in their entirety.

Figure 4:
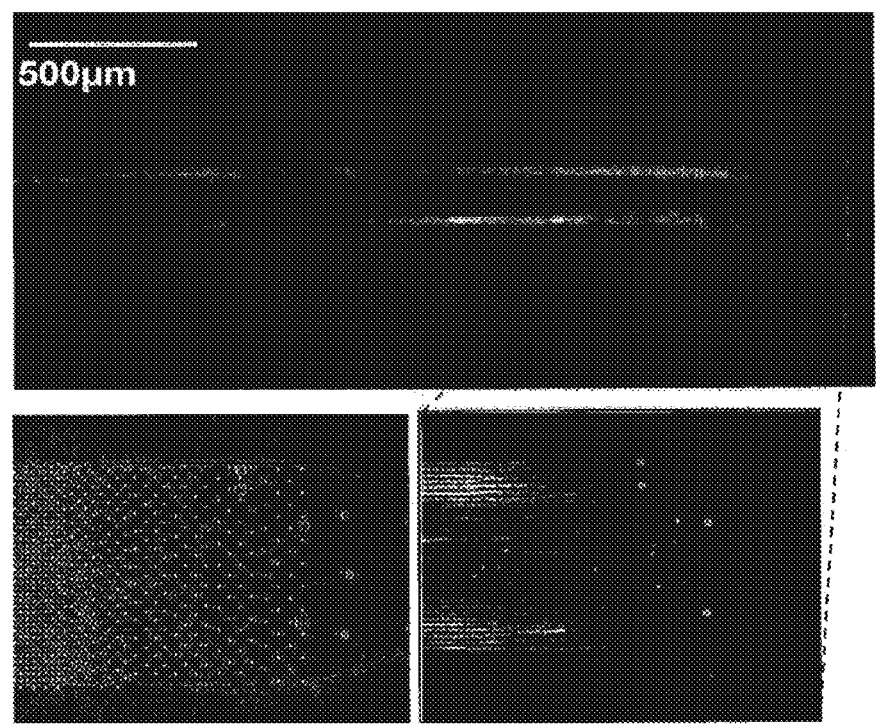
FIG. 4: Fluorescent microscopy images of long DNA strands extracted from four cells. Individual DNA fragments immobilized in one embodiment of the micropillar array of the present invention are clearly visible (top and bottom right image). A blown-up view (bottom right image) shows the position of the 4 cells (white dots) before lysis and the DNA strands being extracted from the cells after lysis. A photomicrograph of the micropillar array of this embodiment of the microfluidic device of the present invention is also shown (bottom left image), with the 4 trapped cells clearly visible.
Figure 5:
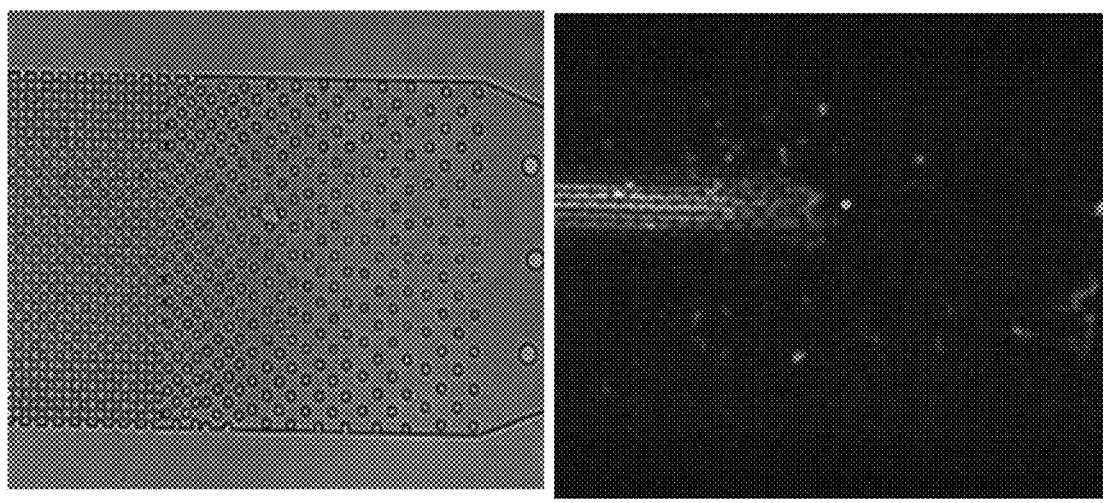
FIG. 5: Bright-field image of a single cell before lysis (left image) and fluorescence image of DNA strands extracted from a single cell (right image).
Figure 6:
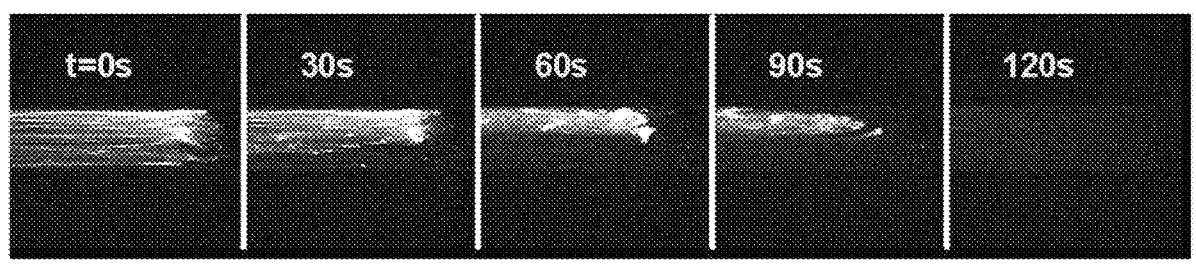
FIG. 6: Time series images of DNA strands undergoing enzymatic fragmentation.
Figure 8:
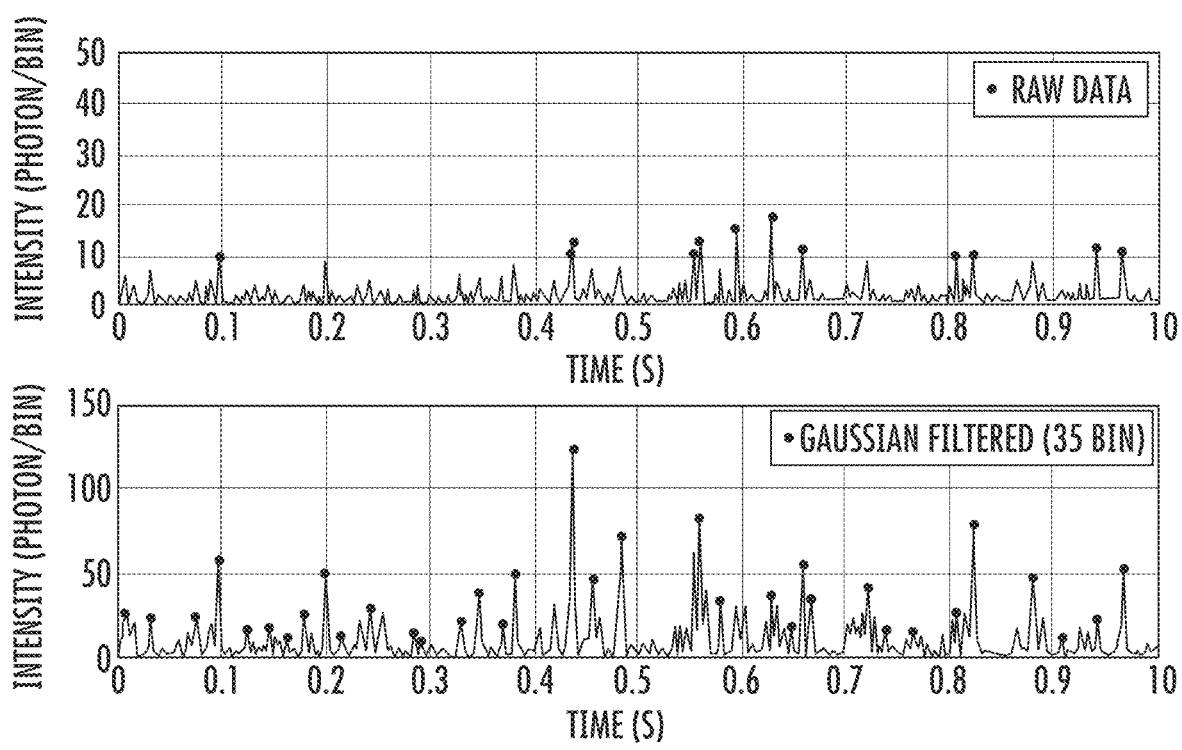
FIG. 8: Plot of the fluorescence intensity as a function of time showing peaks corresponding to individual DNA fragments (extracted from ~100 cells) of various sizes flowed through one embodiment of the nanofluidic device of the present invention and detected one molecule at a time. Raw data is shown (top row) and Gaussian Filtered data is shown (bottom row).

Without meaning to limit the scope of the present invention, in one embodiment, the device of the present invention can operate in the following way. The cells to be analyzed are injected into the input channel, and drawn under constant flow into a tapered array of micropillars in which they become immobilized by size exclusion as shown in FIG. 3. In this particular embodiment, the tapered-array design with progressively decreasing spacing between microposts (also referred to as micropillars) prevents channel clogging when larger numbers of cells and other debris are present. The captured cells are lysed with an appropriate solution, e.g., a solution containing 1% sodium dodecyl sulphate (SDS) in TE buffer. Long strands of genomic DNA released from the cells become entangled in the array of microposts and immobilized by hydrodynamic flow. The pressure driven flow is sufficiently slow so that no DNA shearing occurs or is at least substantially prevented. Immobilized genomic DNA is then rinsed and purified by flowing Proteinase K and Ribonuclease through the microchannels to remove histone proteins and RNA possibly bound to DNA strands. As mentioned earlier, thorough removal of the cellular debris can be important for the subsequent single-molecule studies as the labeled fragment could interfere with the analysis. Immobilized DNA strands extracted from four immobilized cells and from a single cell stained with PICOGREEN® fluorescent dye are shown in FIG. 4 and FIG. 5, respectively. Purified DNA is released from the device by enzymatic digestion with restriction endonucleases (e.g., BAM HI). The digestion process is captured in FIG. 6. The purified and fragmented DNA is collected in the output port of the microfluidic device which serves as the input port of the nanofluidic device used for single molecule analysis of DNA fragments as shown schematically in FIG. 7. The fragments can be driven electrophoretically through the nanofluidic device by applying voltage (e.g., 50V) across the nanochannel and analyzed one molecule at a time by observing single-molecule fluorescence. The plot in FIG. 8 shows fluorescence intensity peaks that correspond to individual DNA fragments flowing through the channel.

EXAMPLES

The following examples are intended to illustrate particular embodiments of the present invention, but are by no means intended to limit the scope of the present invention.

Example 1

Integrated Microfluidic Device for DNA Extraction, Purification and Single-Molecule Fluorescence Analysis This example describes one embodiment of a microfluidic device of the present invention for use in, inter alia, extracting, isolating, and analyzing DNA from cells.

A polydimethylsiloxane (PDMS) microfluidic device for extraction and purification of genomic DNA from small cell populations was developed. MO-91 cells (hematopoietic stem cells infected with myeloid leukemia) were trapped in a two-dimensional array of micropillars in a microfluidic channel and lysed in sodium dodecyl sulfate (SDS) buffer. Long DNA strands released from the lysed cells remained immobilized in the microarray by hydrodynamic forces while the cellular debris was washed away. The purified DNA was then released from the microarray by enzymatic fragmentation under continuous fluidic flow and collected for off-chip analysis by gel electrophoresis and fluorospectrometry. Greater than 95 percent (>95%) efficiency was obtained of genomic DNA recovery from less than 100 cells.

The microfluidic device was integrated with a single chromatin-molecule analysis in nanofluidic device. Enzymatically digested DNA fragments released from the microfluidic device were driven electrophoretically through a nanofluidic channel and observed one molecule at a time. The integrated device will ultimately facilitate analysis of biomolecules extracted from rare cancer cells by allowing genome-wide mapping of epigenetic marks and provide insight into how these marks vary in response to environmental changes and disease progression.

1.1—Device Concept

The technique of extraction and purification of DNA by physical trapping in tapered arrays of micropillars by microfluidic flow explored herein is fundamentally different from the alternative approaches which rely on electrostatic interactions between DNA and the microchannel walls or biochemically functionalized microparticles. In the microfluidic device of the present invention, long strands of genomic DNA released from the lysed cells become immobilized in the tapered array of microposts by hydrodynamic flow because of their large size while the rest of the cellular contents are washed away by pressure-driven flow. The flow rate is optimized so that the trapped DNA strands are not sheared in the PDMS microfluidic channel. Thorough removal of the cellular debris is important for the subsequent single-molecule studies as the labeled protein and lipid fragments can interfere with the analysis. The method of separation by hydrodynamic forces allows separation of genomic DNA not only from proteins and lipids which are primary components of the cell lysate, but also from other nucleic acids such as mitochondrial DNA and RNA. This cannot be achieved with the alternative extraction methods. Purified genomic DNA can be labeled under continuous flow and the unbound dye can be removed from the buffer which will facilitate single-molecule analysis in the nanochannels using fluorescent microscopy techniques by reducing background fluorescence.

1.2—Device Design and Fabrication

A microfluidic device as shown schematically in FIG. 1 was fabricated in polydimethylsiloxane (PDMS) using standard soft-lithography and mould-replica techniques and bonded onto a fused silica substrate. In the embodiment of this example, the relevant dimensions of the microfluidic device included an input channel width of about 50-100 µm, a channel depth of about 20 µm, a cell capture region width of about 200-500 µm, a channel length of about 13 mm, a micropillar width of about 4 µm, and a smallest gap between pillars of about 1.5 µm. The microchannels hold ~50 nL of fluid. Photomicrographs of fabricated devices with micropillar arrays are presented in FIG. 2. Tapered microarrays with various dimensions were fabricated to accommodate different populations of cells. The explored designs hold up to 500 cells.

1.3—Device Operation

MO-91 cells (hematopoietic stem cells infected with myeloid leukemia) were trapped in a two-dimensional array of micropillars in a microfluidic channel. The cells were injected into the input channel, and drawn under constant flow into the tapered array of micropillars in which they become immobilized by size exclusion as shown in FIG. 3. The microarray design with progressively decreasing spacing between microposts prevents channel clogging when larger numbers of cells and other debris are present in the growth medium. The captured cells were lysed with a solution containing 1% sodium dodecyl sulfate (SDS) in Tris-EDTA buffer. Long strands of genomic DNA released from the cells become entangled in the array of microposts and immobilized by hydrodynamic flow. The pressure driven flow is sufficiently slow so that DNA does not sheer. After the lysis, immobilized genomic DNA is then rinsed and purified by flowing proteinase K and ribonucleases through the microchannels to remove histone proteins and RNA possibly bound to the combed DNA strands. Thorough removal of the cellular debris is important for the subsequent single-molecule studies as the labeled fragment could interfere with the analysis. Immobilized DNA strands extracted from four immobilized cells and from a single cell stained with PICOGREEN® fluorescent dye are shown in FIG. 4 and FIG. 5, respectively. Purified DNA is released from the device by enzymatic digestion with restriction endonucleases (Bam HI and Hind III). The digestion process is captured in FIG. 6. All purified DNA is released from the microarray into the collection reservoir within 2 minutes.

The digested DNA was collected into small elution volumes (~20 µL) for off-chip analysis with gel electrophoresis and fluorospectrometry (NANODROP 3300 fluorospectrometer). The cells captured in the array of micropillars were counted and the amount of the DNA was determined by assuming 6.6 pg of DNA in each cell. These approximate fluorospectrometric measurements indicate the collection and purification of >95% of genomic DNA. The small losses can be attributed to DNA bound to the walls of the Eppendorf vials and microfluidic tubing.

1.4—Integrated Microfluidic-Nanofluidic Device for DNA Extraction and Single-Molecule Analysis The purified and fragmented DNA was also collected in the output port of the microfluidic device which was aligned with the input port of the nanofluidic device used for single molecule analysis of DNA fragments. The integrated nano-microfluidic device is shown schematically in FIG. 7. The nanofluidic portion was fabricated in fused silica using standard optical lithography and silica wafer bonding as described in Ref. A1. The fragments are driven electrophoretically through the nanofluidic device by applying voltage (50V) across the nanochannel and analyzed one molecule at a time by observing single-molecule fluorescence. The plot in FIG. 8 (bottom portion) shows fluorescence intensity peaks that correspond to individual DNA fragments flowing through the microchannel.

The extracted DNA flows from the microfluidic channel directly into nanofluidic component and is never removed from the integrated nano/microfluidic platform which prevents inadvertent losses during sample manipulations. The device should thus be suitable for genome-wide analysis of individual single cells.

Example 2

Microfluidic Extraction, Elongation, and Hybridization of Human Chromosomal DNA From Single Cells This example reports on one embodiment of the present invention and in particular a microfluidic device for extraction, purification, elongation, and hybridization of human chromosomal DNA from single cells. Single cells were captured in a two-dimensional array of pillars in a microfluidic polydimethylsiloxane (PDMS) channel and lysed with an ionic surfactant. Megabase-long DNA strands released from the cells were trapped in the micropillar array and elongated under hydrodynamic flow up to 27 mm in length. The physical trapping of the chromosomal DNA allows the efficient removal of other cellular components from the solution by simple washing. The elongated DNA extracted from single cells was hybridized using FISH techniques. DNA from small cell populations was released from the device by enzymatic fragmentation with restriction endonucleases under continuous flow and collected for off-chip evaluation of the extraction efficiency. Fluorospectrometric measurements indicate that the microdevice extracts essentially all of the genomic DNA.

Introduction

Genome-wide analysis of single cells is important in life science research and modern medicine in applications ranging from cancer diagnosis to understanding tissue development. Microfluidic devices have been explored as a promising platform for single cell studies, providing superior handling of minute sample and reagent volumes in engineered microstructures (Refs. 1-6). Microfluidic devices operate automatically in an enclosed system, thereby reducing the chance for human error and cross contamination. Furthermore, the low reagent volumes combined with high rates of reaction at the microscale give microfluidic devices a distinct advantage in lowering both the time and cost of operation. Isolation of nucleic acids from biological samples is a required step for every type of genetic analysis. While numerous extraction methods have been explored (Refs. 7-12), it remains rather challenging to isolate and analyze genomic DNA from small cell populations and single cells. Traditional microfluidic platforms utilize solid phase extraction (SPE), a method dependent upon the binding of DNA to solid phase matrices such as silica (Ref 13) or functionalized magnetic microparticles (Ref. 14), for extraction of nucleic acids from cell lysates. Various surface treatment protocols have been developed to enhance the affinity of the surface of microdevices to nucleic acids (Refs. 10, 15), however, this binding affinity is extremely sensitive to factors such as pH, temperature, and buffer compositions which often require dynamic control in order to minimize DNA losses. Additionally, other components of the cellular lysate may potentially inhibit the intended binding reactions. For example, negatively charged proteins in the cell lysate can decrease the efficiency of extraction by interacting with positively charged surfaces within the device. Even when the process is optimized, it is difficult to ensure that all of the DNA fragments are adsorbed on the solid phase matrix and that the whole genome is represented in purified extracts. An appreciable fraction of genomic DNA is often lost during the purification process when the cell debris is washed away. Additional DNA losses can be caused by incomplete elution. As a result, the current state-of-the-art microfluidic devices for DNA separation from cell lysates exhibit rather modest extraction efficiencies of 60-90% (Ref. 8). This level of extraction is sufficient for genetic analysis of large cellular populations as multiple copies of every gene are present within the extract, which statistically guarantees complete genome coverage, but such collection losses are unacceptable when single-copy genes in a single cell need to be investigated. Even with improved yields, it is fundamentally difficult to apply SPE techniques to single cell studies due to manufacturing complexities and technical challenges associated with manipulation of small volumes of fluids. Current microfluidic devices with such capabilities rely on complicated fluidic networks of channels, valves, reaction chambers (or droplets) for storing, transporting, and mixing picoliter volumes of sample and reagents (Refs. 3-4). The complexity of these devices has so far prevented their widespread adoption by clinicians and researchers.

This example describes a simple, valveless, two-port microfluidic device capable of highly-efficient isolation and fluorescent analysis of DNA from single cells by trapping and elongating long strands of human genomic DNA in two-dimensional arrays of micropillars. The flow of DNA through arrays of obstacles involves collisions which impede its propagation and can result in immobilization if the size of the fragments is sufficiently large (Ref. 16). Although DNA transport in obstacle arrays have been studied extensively for fragment size separation (Refs. 17-18), hydrodynamic entrapment is yet to be used to extract and purify human chromosomal DNA from cell lysates. This approach is fundamentally different from the conventional microchip-based SPE as well as from physical filtration through nanopores which causes DNA shearing and often results in device failure though clogging (Ref. 19). In the microfluidic device presented here, long strands of human chromosomal DNA released from cells through chemical lysis are looped around PDMS micropillars and are physically retained while the remaining cellular contents are washed away under hydrodynamic flow. In this manner, random DNA fragmentation is minimized by operating at low flow rates and hydrodynamic entrapment of DNA in non-functionalized obstacle arrays allows separation of large genomic DNA from a multitude of cellular debris such as proteins and lipid membrane fragments as well as from much smaller mitochondrial DNA and RNA due to the inbuilt size screening. This physical extraction method provides several unique capabilities that make it attractive for genetic and epigenetic analysis of DNA contents of single cells. For example, the device can be used to linearize largely intact human chromosomal DNA for genome-wide analysis by fluorescent in-situ hybridization (FISH) of specific sequences (Ref. 20), a process that has been successfully performed so far only on significantly shorter fragments of combed (Refs. 21-22) and hydrodynamically (Ref. 23) extended DNA. Unlike combed nucleic acids, hydrodynamically trapped DNA in the microchannel is not in direct contact with solid surfaces except at the micropillars, thus improving the binding of site-specific fluorescent tags and reducing hybridization times. The suspended DNA can also be released from the microarrays by enzymatic digestion with restriction endonucleases and subsequently collected for downstream analysis of the digestion product in nanofluidic channels by DNA fragment sizing (Ref. 24) or multicolor fluorescence (Ref. 25). Genome-wide analysis of DNA contents of single cells could thus be performed one fragment at a time, without the need for amplification. To demonstrate the applicability and utility of the presented microdevice regarding single cell analysis, the device was used to extract, purify, elongate, and hybridize DNA from single human cells.

Materials and Methods 2.1—Device Design and Fabrication

Microfluidic devices were fabricated in polydimethylsiloxane (PDMS) (SYLGARD® 184 elastomer, Dow Corning; Midland, MI) using standard soft-lithography and mold-replica techniques. Briefly, to fabricate the master molds, Microposit S1813 photoresist (Shipley; Marlborough, MA) was spun on silicon on insulator (SOI) wafers (Ultrasil; Hayward, CA) and exposed by UV contact lithography (EV 620, EVG Group; Albany, NY). The exposed resist was development in 726MIF developer (Microchemicals) and the pattern was transferred into the 20 µm-thick top silicon layer by Bosch process in a Unaxis SLR 770 deep reactive ion etching system (Unaxis USA Inc.; St. Petersburg, FL). A monolayer of (1H,1H,2H,2H-Perfluorooctyl)Trichlorosilane was deposited on the etched wafers in a MVD 100 molecular wafer deposition system (Applied Microstructures; San Jose, CA) to prevent sticking of the PDMS to the mold. PDMS base resin was mixed with the curing agent at a 10:1 ratio, degassed under vacuum at room temperature, poured onto the master, and cured for 45 minutes at 150° C. The ellastomer casting was then peeled off the mold and access holes to the input and outputs of the microchannels were created with a 1.5 mm biopsy punch (Sklar Instruments, West Chester, PA). To complete channel fabrication, the patterned PDMS was treated with oxygen plasma for 1 minute and bonded to a 170-µm thick fused silica wafer (Mark Optics; Santa Ana, CA). FIG. 9 shows the device schematic and photomicrograph of a section of the fabricated microchannels supporting the random array of micropillars. The microchannels are 240 µm wide, 20 µm deep and up to 70 mm long. The array of microposts (5 µm wide and 20 µm tall) was designed with a gradient in spacing to create a solid obstacle for cell capture. The average gap between the microposts varies continuously from 15 µm to 2 µm along the channel. Though intended primarily for single cell analysis, the device can hold up to ~20 cells with a broad size distribution without clogging the channel. The extraction method can be scaled up to perform extraction of larger quantities of DNA from thousands of cells by broadening the microchannels. The 500 µm-long array of micropillars also provides a solid phase matrix for immobilization of chromosomal DNA. Random placement of micropillars maximizes the number of collisions of DNA with solid surfaces, thereby preventing DNA strands from easily slipping throught the structure. Linear arrays of micropillars spanning the channel width, spaced by 100 µm throughout the microchannel, were also incorportated to provide support for the suspended DNA via weak steric interactions which helps prevent shearing of megabase long strands. To avoid strong electrostatic adsorption of DNA to the channel walls and the micropillars, the channels were primed and blocked with a 1% (wt) solution of polyvinylpyrollidone (PVP) (Fluka; St. Louis, MO) and 1% (wt) bovine serum albumin (BSA) (Sigma-Aldrich) in tris-EDTA (TE) (10 mM Tris-HCl, 20 mM EDTA, 100 mM NaCl) buffer for 5 hours. The coated microchannels were rinsed with Tris-EDTA (TE) buffer for 1 hour at a rate of 30 nl/min in room temperature prior to experimentation.

2.2—Cell Culture

M0-91 (hematopoietic stem cells infected with myeloid leukemia) cells were cultured in Dulbecco's Modified Eagle Medium (DMEM) (Invitrogen) at 37° C., 5% $CO_2$ in T25 flask. DMEM cell culture media was supplemented with DMEM High Glucose 1× (Gibco 11965), non-essential Amino Acids, 100× (Gibco 11140), Sodium Pyruvate, 100 mM, 100× (Gibco 11360), Penicillin Streptomycin, 100× (Gibco 15140), HEPES Buffer Solution, 1M (Gibco 15630), and 2-mercaptoethanol (1:100 dilution with H2O) (Sigma 63689). Cells were split every 3 days into equal volumes of fresh media.

2.3—Fluorescence Imaging and Microfluidic Flow

The microfluidic device for DNA extraction was placed on an in-house fabricated heating stage mounted on an Olympus IX70 inverted microscope (Olympus; Center Valley, PA). Stage temperature was controlled with a Model 1146D VWR heated/refrigerated recirculator (Randor, PA). The microscope used for sample visualization was equipped with a 10× objective (Plan APO, N.A. 0.45); a 20× objective (Plan APO, N.A. 0.60); a 60× water immersion objective (Olympus UPlanSApo 60×/1.2 W)); an X-Cite® 120 mercury light source (Lumen Dynamics; Mississagua, ON); a filter cube (exciter/emitter 485/535 nm; Chroma, Bellow Falls, VT); and a Cascade II charge-coupled device (CCD) camera (Photometrics; Tucson, AZ). A 100 mL gas-tight syringe (Hamilton; Reno, NV) was connected to the microchannel via PEEK™ polymer tubing (I.D.=254 µm, O.D.=1.58 mm) which was inserted into the output of the microdevice. Cells and reagents were delivered into the microdevice by pressure-driven flow created by refilling the syringe with a PHD 2000 pump (Harvard Apparatus; Holliston, MA) at a 30 nL/min flow rate. DNA in the microchannels was stained with PICOGREEN® dsDNA intercalating fluorescent dye (Invitrogen, Carlsbad, CA) intercalating dye and the individual steps of the extraction process were monitored with the fluorescence setup.

2.4—Cell Capture and Lysis

A solution containing M0-91 cells suspended in original culturing media was injected into the input port of the microdevice and drawn under a constant flow into a random array of micropillars in which the cells become immobilized as shown in First Step A of FIG. 10. The pressure driven flow was interrupted when a single cell was captured in the microarray and the input port was repeatedly rinsed to remove any remaining cells. The microchannel with a single immobilized cell was then rinsed with a TE buffer (10 mM Tris-HCl, 20 mM EDTA, 100 mM NaCl) to remove residues of the cell culture growth medium and lysed with a solution containing 1 (wt) % sodium dodecyl sulfate (SDS) in the same buffer (see Second Step B of FIG. 10). Long strands of the released chromosomal DNA became entangled in the microchannel under hydrodynamic flow while the unwanted components of the cell lysate such as proteins, lipid membrane fragments, non-genomic DNA, and RNA were washed away (see Second Step B of FIG. 10).

2.5—DNA Purification and Visualization

The immobilized genomic DNA was rinsed and purified by flowing a buffer containing proteinase K (Qiagen; Valencia, CA) through the microchannels to remove any remaining histone proteins bound to the stretched DNA strands. Thorough removal of the cellular debris and the lysis agent is often desirable for sample preparation to prevent interference with downstream processes such as polymerase chain reaction (PCR) amplification or single-molecule fluorescence analysis (Refs. 24-25). The trapped chromosomal DNA was fluorescently labelled using the nucleic acid stain PICOGREEN® fluorescent dye and visualized by fluorescence microscopy setup described in Fluorescence Imaging and Microfluidic Flow section above (see Third Step C of FIG. 10). Background fluorescence inside the microchannel was dramatically reduced by washing off the unbound dye surrounding the suspended DNA.

2.6—Chromosomal Painting

To show selective genomic DNA hybridization, chromosome 17 was labelled with whole chromosome paints (Human IDetect FISH Probes, IDlabs Inc.; London, ON). Genomic DNA and chromosome 17 probe were co-denatured in 2×SSC buffer (30 mM citrate, pH 7, 300 nM NaCl) and 50% formamide at 90° C. for 5-10 minutes. Hybridization was performed at 40° C. for 1-2 hours. Excess probe was washed away with 2×SSC buffer at room temperature. TE buffer (10 mM Tris, pH 8.0, 1 mM EDTA) was used for imaging.

2.7—DNA Release and Off-Chip Fluorescence Analysis

Because the extraction mechanism is based on DNA immobilization by the physical action of looping around micropillars there is a possibility that some of the DNA strands escape by shearing and channeling through the obstacle array. To verify that this does not result in a significant DNA loss during the lysis and purification steps, the suspended DNA strands were fragmented, collected, and quantified by fluorospectrometry. Fluorescently labelled genomic DNA suspended in the microchannel was released from the device by enzymatic digestion with BamHI (Invitrogen) restriction endonuclease as illustrated in Fourth Step D of FIG. 10. To optimize the digestion process, the microchannels were heated to 37 C° prior to the introduction of restriction enzymes. The fragmentation process was monitored in real time by observing PICOGREEN® fluorescent dye fluorescence with a CCD camera. Since the total DNA content of a single human diploid cell (~6.6 pg) (Ref. 26) is not sufficient for reliable off-chip fluorospectrometric quantification, the analysis was performed with larger quantities of M0-91 cells loaded into the obstacle array. The DNA trapped in the microchannel was eluted at 100 nL/min flow into <200 nL of 1×Digestion Buffer K (Invitrogen). Sample dilutions were controlled simply by adjusting the flow rates. To facilitate off-chip sample manipulation, the released DNA was diluted further by flowing additional 20 μL of buffer through the microdevice. The total extract was collected in the polymer tubing that connects the syringe to the output channel. Once filled with fragmented DNA, the tubing was disconnected from the device and its contents were injected into a 0.2 ml Eppendorf tube for off-chip quantification. Thus, purified DNA from the known number of cells was suspended in 20 μL of digestion buffer. Solutions containing DNA extracts obtained from the microchannels were diluted with an equal amount of PICOGREEN® fluorescent dye and their fluorescence intensity was measured using a NANODROP 3300 fluorospectrometer (NanoDrop; Wilmington, DE). The instrument only requires a small amount of sample per measurement (1 to 2.5 μL), thereby allowing multiple measurements (N=10) to be taken for each extract.

Results

2.8—DNA Extraction From a Single Cell

The microfluidic device described herein is designed to capture individual cells in an array of micropillars, perform lysis, extraction, purification, and then linearize the released human chromosomal DNA. The rationale behind using micropillar obstacles is that chromosomal DNA is significantly larger than the remaining cell contents and can be therefore separated from the lysate by size. Because DNA is delivered into the microdevice device in a living cell and the extraction is performed at very low flow rates, the DNA fragmentation throughout the process is minimized. As noted above, device operation is illustrated schematically in FIG. 10. Briefly, intact DNA confined in the cell is delivered into the micropillar arrays by hydrodynamic flow. The captured cell is chemically lysed with a surfactant that dissolves the cell wall and the nuclear membrane thereby releasing the DNA into the lysis solution. The surfactant also gradually destroys the higher-order chromatin structure by denaturing and stripping off histone proteins. The hydrodynamically-driven DNA collides immediately with the micropillars and loops around them in a rope-over-pulley fashion. Dense arrays of randomly spaced micropillar obstacles were chosen to maximize the number of collisions encountered by the unwrapping DNA and to fan out the individual strands of chromosomal DNA as they unwind. This helps to separate and spread individual strands of DNA in the microchannel. DNA migration under hydrodynamic flow is inhibited by weak steric interactions with the non-functionalized micropillars and with other strands of chromosomal DNA.

FIG. 11A shows an image of a cell trapped in the microarray by micropillars of an embodiment of the microfluidic device of the present invention. FIGS. 11B-11C show fluorescent images of DNA strands released from a single M0-91 cell. The DNA strands extend ~27 mm into the channel, which is significantly shorter than the length of chromosomal DNA in B-form which ranges from 17 mm (chromosome 21) to 85 mm (chromosome 1) (Ref. 26). This suggests that the observed strands are either mutliply-folded or they have been sheared under flow and escaped from the microarray. To investigate the two scenarios in more detail, the extraction efficiency was determined using off-chip fluorospectrometry and a single chromosome pair (chromosome 17) was labelled with chromosome paints and imaged with high numerical aperture objectives.

FIGS. 12A-12D show fluorescent images of selectively labelled chromosomes 17. The images reveal that the chromosomes are intact, multiply folded, looped around dozens of micropillars, and extended over 10 mm into the microchannel. This simple experiment indicates that fluorescent hybridization can be carried out on stretched DNA without fragmenting hundreds of megabases long strands. The capability to unravel and hybridize long chromosomal DNA is essential for genome-wide mapping of medically relevant chromosomal aberrations that adversely affect cell cycle regulation and contribute to cancer origination and development. Since such abnormalities often span over several megabases or more of DNA (Ref. 27), they should be imaged and mapped on unfragmented, high molecular weight genomic DNA.

2.9—Off-Chip Quantification

Figure 13A:
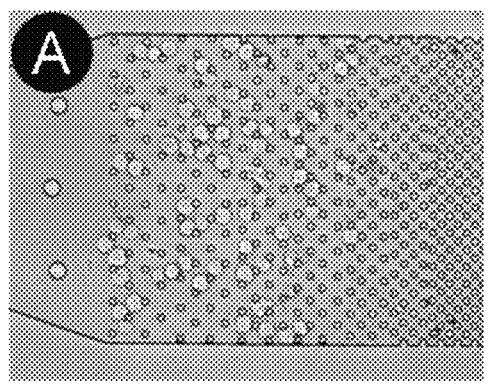
FIGS. 13A-13D.
Figure 13B:
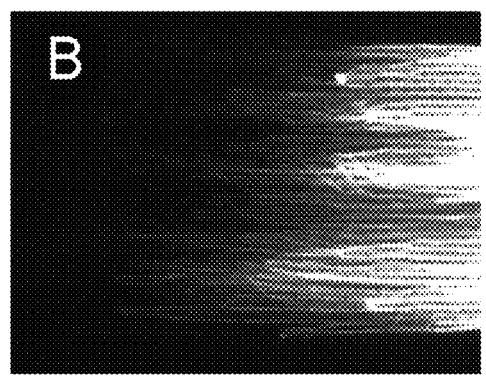
Figure 13C:
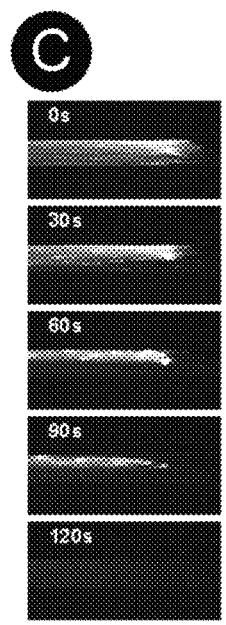

To determine the extraction efficiency of the microfluidic device, multiple devices were loaded with up to 83 M0-91 cells from which chromosomal DNA was then isolated following the single-cell procedure described earlier. Multiple cells were used because the small amount of genomic DNA contained in a single cell is insufficient for reliable fluorospectrometric quantification. The micropillar array design was modified for these measurements to accommodate larger cell populations. A semi-ordered array with gradually decreasing spacing between the micropillars shown in FIG. 13A was used. Purified DNA was released from the devices via enzymatic digestion described in DNA Release and Off-Chip Fluorescence Analysis section of this example. FIG. 13B shows a fluorescent image of the released DNA. As illustrated in the sequence of images in FIG. 13C, all DNA was released from the microchannel into the collection reservoir under 100 nL/min flow within 2 minutes.

Figure 13D:
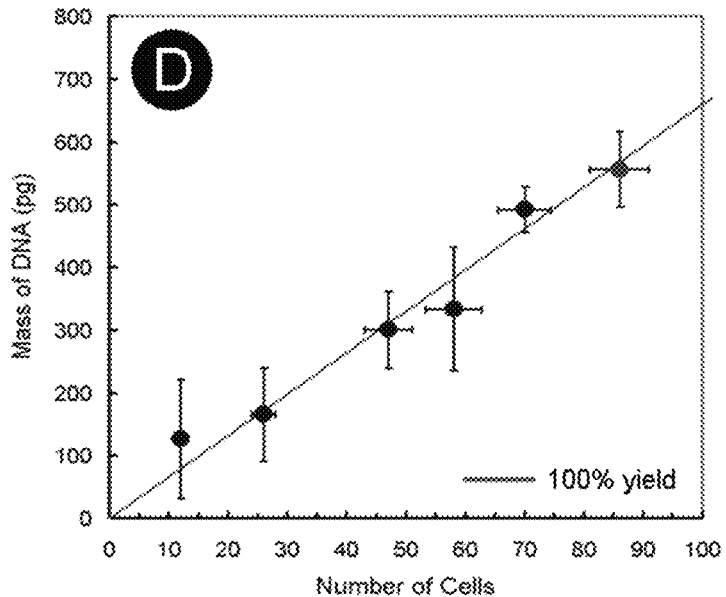

FIG. 13D compares the amounts of DNA extracted from six devices loaded with different numbers of M0-91 cells. The fluorescence intensity of the extracts measured with a NANODROP 3300 fluorospectrometer was directly proportional to the number of cells. The mass of the extracted DNA was quantified by calibrating the fluorescence measurements with bacteriophage T4 DNA standards and the total mass of extracted DNA was calculated from the fluorescent intensity signal. For comparison, the solid line in FIG. 13D shows the expected amount corresponding to 100% yield, assuming a genomic DNA content of 6.6 pg per each human diploid cell. The uncertainty in cell counts is caused by the presence of dead and dying cells and other debris in the growth medium which makes cell identification and counting in micropillar arrays difficult. Only healthy, intact cells were considered in the calculation of the extraction efficiency because the DNA from dead or dying cells is already fragmented and the strands are too short to get captured in the microarray by looping around micropillars. In a control experiment, no DNA strands were observed in the obstacle array when a population of dead M0-91 cells were immobilized and lysed in the microchannel. The extraction efficiency was calculated by comparing the measured amount of collected DNA to the maximum possible amount based on the cell counts. Large vertical error bars reflect the fact that it is rather difficult to obtain a consistent fluorescent background when dealing with sub-nanogram quantities of DNA. Nevertheless, the average measured amounts of collected DNA fall close to the perfect yield line indicating that only negligible quantities of DNA are lost during the highly-efficient physical extraction process. The microdevices extract essentially 100% of genomic DNA from small cell populations, outperforming both macroscopic and microchip-based SPE methods.

Conclusion

The entrapment and chemically-induced lysis of human cells in an array of microposts was shown to be a highly-effective technique for trapping, purifying, and elongating human genomic DNA on a chip. Unlike conventional microchip-based extraction techniques, the presented physical capture mechanism does not depend on biochemical and electrostatic binding interactions between nucleic acids and functionalized surfaces. It produces largely intact, linearized DNA which can be hybridized and used for genome-wide mapping of chromosomal aberrations by FISH techniques. The extracted DNA can be also released from the microarrays by sonication or enzymatic digestion into small elution volumes for downsteam genome-wide analysis. Essentially 100% of genomic DNA can be extracted using this method, rendering the extraction strategy particularly suited for genomic analysis of DNA from small cell populations and individual cells without the need for amplification. For example, we envision the PDMS device to be integrated with microfluidic platforms for isolation of rare circulating tumor cells or stem cells that are difficult to study with ensemble-based methods (Ref. 28). The DNA from captured cell can then be analyzed downstream with single-molecule fluorescence in nanofluidics (Refs. 24-25) to characterize its genetic and epigenetic states.

References in This Example 2

Citation of a reference in this Example 2 shall not be construed as an admission that such reference is prior art to the present invention. All references cited in this Example are hereby incorporated by reference in their entirety. Below is a listing of various references cited in this Example:

(1) R. N. Zare and S. Kim, in *Annual Review of Biomedical Engineering*, Vol 12, Annual Reviews, Palo Alto, 2010, vol. 12, pp. 187-201.
(2) A. R. Wheeler, W. R. Throndset, R. J. Whelan, A. M. Leach, R. N. Zare, Y. H. Liao, K. Farrell, I. D. Manger and A. Daridon, *Anal. Chem.*, 2003, 75, 3581-3586.
(3) A. K. White, M. VanInsberghe, O. I. Petriv, M. Hamidi, D. Sikorski, M. A. Marra, J. Piret, S. Aparicio and C. L. Hansen, *Proceedings of the National Academy of Sciences of the United States of America*, 2011, 108, 13999-14004.
(4) J. Clausell-Tormos, D. Lieber, J.-C. Baret, A. El-Harrak, O. J. Miller, L. Frenz, J. Blouwolff, K. J. Humphry, S. Koster, H. Duan, C. Holtze, D. A. Weitz, A. D. Griffiths and C. A. Merten, *Chemistry & Biology*, 2008, 15, 427-437.
(5) G. Ocvirk, H. Salimi-Moosavi, R. J. Szarka, E. A. Arriaga, P. E. Andersson, R. Smith, N. J. Dovichi and D. J. Harrison, *Proceedings of the Ieee*, 2004, 92, 115-125.
(6) Y. Marcy, T. Ishoey, R. S. Lasken, T. B. Stockwell, B. P. Walenz, A. L. Halpern, K. Y. Beeson, S. M. D. Goldberg and S. R. Quake, *PLoS Genet.*, 2007, 3, 1702-1708.
(7) M. B. Johns and J. E. Paulusthomas, *Anal. Biochem.*, 1989, 180, 276-278.
(8) J. Kim, M. Johnson, P. Hill and B. K. Gale, *Integr. Biol.*, 2009, 1, 574-586.
(9) K. A. Wolfe, M. C. Breadmore, J. P. Ferrance, M. E. Power, J. F. Conroy, P. M. Norris and J. P. Landers, *Electrophoresis*, 2002, 23, 727-733.
(10) C. R. Reedy, C. W. Price, J. Sniegowski, J. P. Ferrance, M. Begley and J. P. Landers, *Lab Chip*, 2011, 11, 1603-1611.
(11) C. W. Price, D. C. Leslie and J. P. Landers, *Lab Chip*, 2009, 9, 2484-2494.
(12) S. M. Berry, E. T. Alarid and D. J. Beebe, *Lab Chip*, 2011, 11, 1747-1753.
(13) R. Boom, C. J. A. Sol, M. M. M. Salimans, C. L. Jansen, P. M. E. Wertheimvandillen and J. Vandernoordaa, *J. Clin. Microbiol.*, 1990, 28, 495-503.
(14) M. C. Breadmore, K. A. Wolfe, I. G. Arcibal, W. K. Leung, D. Dickson, B. C. Giordano, M. E. Power, J. P. Ferrance, S. H. Feldman, P. M. Norris and J. P. Landers, *Anal. Chem.*, 2003, 75, 1880-1886.
(15) D. S. W. Park, M. L. Hupert, M. A. Witek, B. H. You, P. Datta, J. Guy, J. B. Lee, S. A. Soper, D. E. Nikitopoulos and M. C. Murphy, *Biomedical Microdevices*, 2008, 10, 21-33.
(16) N. P. Teclemariam, V. A. Beck, E. S. G. Shaqfeh and S. J. Muller, *Macromolecules*, 2007, 40, 3848-3859.
(17) W. D. Volkmuth and R. H. Austin, *Nature*, 1992, 358, 600-602.
(18) S. W. Turner, A. M. Perez, A. Lopez and H. G. Craighead, *J. Vac. Sci. Technol. B*, 1998, 16, 3835-3840.
(19) J. Kim and B. K. Gale, *Lab Chip*, 2008, 8, 1516-1523.
(20) H. H. Q. Heng, B. Spyropoulos and P. B. Moens, *Bioessays*, 1997, 19, 75-84.

(21) X. Michalet, R. Ekong, F. Fougerousse, S. Rousseaux, C. Schurra, N. Homigold, M. vanSlegtenhorst, J. Wolfe, S. Povey, J. S. Beckmann and A. Bensimon, *Science*, 1997, 277, 1518-1523.
(22) I. Parra and B. Windle, *Nature Genet.*, 1993, 5, 17-21.
(23) E. Y. Chan, N. M. Goncalves, R. A. Haeusler, A. J. Hatch, J. W. Larson, A. M. Maletta, G. R. Yantz, E. D. Carstea, M. Fuchs, G. G. Wong, S. R. Gullans and R. Gilmanshin, *Genome Res.*, 2004, 14, 1137-1146.
(24) M. Foquet, J. Korlach, W. Zipfel, W. W. Webb and H. G. Craighead, *Anal. Chem.*, 2002, 74, 1415-1422.
(25) B. R. Cipriany, R. Zhao, P. J. Murphy, S. L. Levy, C. P. Tan, H. G. Craighead and P. D. Soloway, *Anal. Chem.*, 2010, 82, 2480-2487.
(26) B. Alberts, *Molecular Biology of the Cell*, Garland Science, New York, 2002.
(27) Y. G. Ji, E. E. Eichler, S. Schwartz and R. D. Nicholls, *Genome Res.*, 2000, 10, 597-610.
(28) S. Nagrath, L. V. Sequist, S. Maheswaran, D. W. Bell, D. Irimia, L. Ulkus, M. R. Smith, E. L. Kwak, S. Digumarthy, A. Muzikansky, P. Ryan, U. J. Balis, R. G. Tompkins, D. A. Haber and M. Toner, *Nature*, 2007, 450, 1235-U1210.

Example 3

Figure 14:
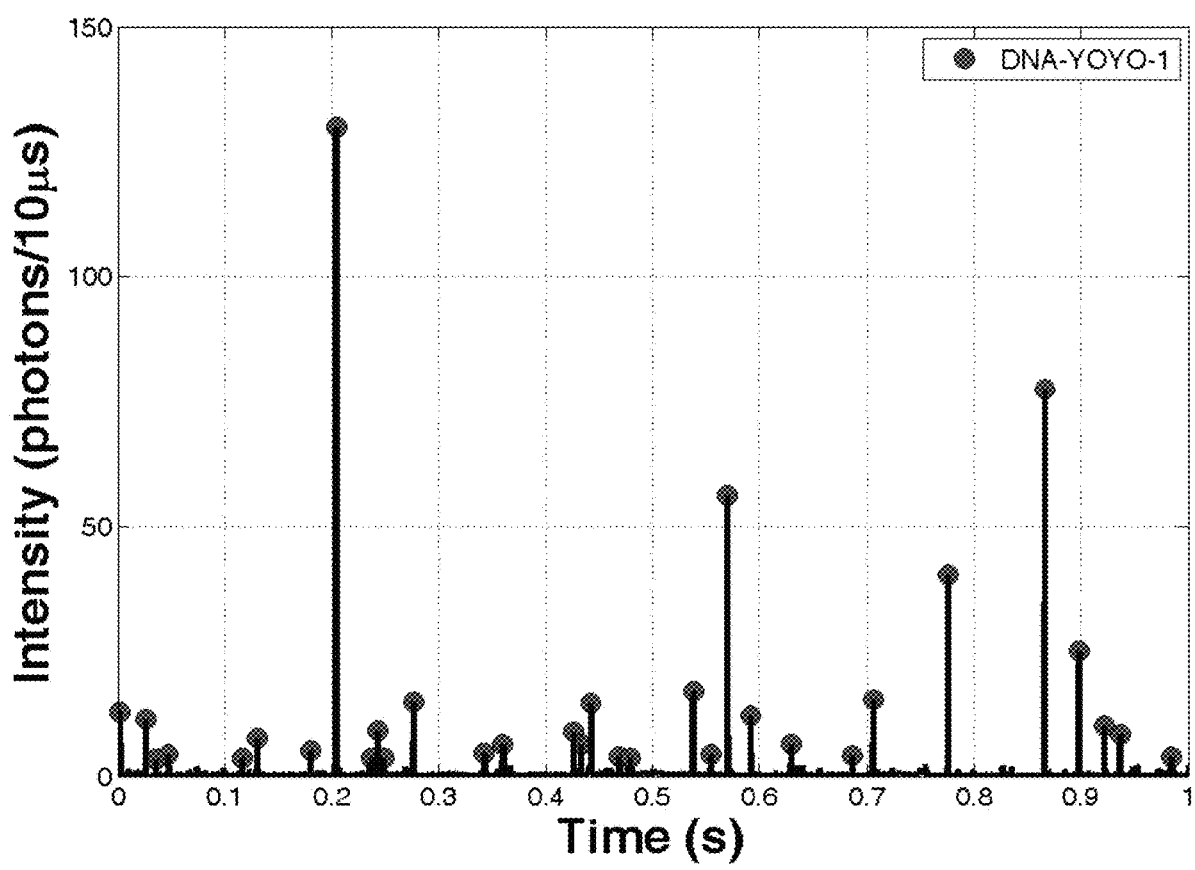
FIG. 14: A chart illustrating a time trace taken from a single cell experiment using human hematopoietic stem cells (MO-91). The data was obtained by using one embodiment of a microfluidic-nanofluidic system of the present invention.

PDMS Microfluidic-Fused Silica Nanofluidic System for Extracting and Analyzing DNA from Human Hematopoietic Stem Cells As shown in FIG. 14, a time trace from a single cell experiment using human hematopoietic stem cells (MO-91) was obtained using a coupled PDMS microchannel/fused silica nanochannel device, which corresponds to one embodiment of a microfluidic-nanofluidic system of the present invention. FIG. 14 illustrates that, using a microfluidic-nanofluidic system of the present invention, one can flow and detect DNA from a single cell into nanochannels, the DNA having been obtained using a PDMS microfluidic device of the present invention. This technique can be used for applications such as intensity/photon count based fragment sizing from single cells, DNA methylation analysis based on restriction enzymes (HPAII and MSPI) or methyl binding domain (MBD), and coincident detection of epigenetic marks from single cells.

The experiment was generally performed as follows: (a) Trap a single cell in the micropillar array. (b) Lyse the cell using 1% sodium dodecyl sulfate (SDS) TE buffer solution at ~10 nl/min. (c) Wash away cell debris at a low flow rate as to not shear the DNA (~20-30 nl/min). Displace approximately 5 ul during this washing step. (d) Flow in a restriction enzyme to break up the DNA (HindIII in this experiment). Flow the restriction enzyme for 1 hr and displace about 1.5 ul of fluid. (e) Increase the flow rate to ~1 ul/min to remove any remaining DNA that may be trapped on the side walls or stuck in the pillars. As can be seen with micrographs, almost all of the DNA leaves with the restriction enzyme and this step is likely unnecessary. Displace about 4 ul of fluid during this step. (f) Remove the tubing from the PDMS and flow the DNA solution into the nanofluidic input. (g) Stain the DNA in the nanofluidic input port for 1-2 hrs. using cyanine dimers high affinity intercalators (Invitrogen e.g. YOYO-1, POPO-1, TOTO-3, etc.). (h) Apply a voltage (50-250V for our devices) to electrophoretically drive the DNA from the input port to the output port in the nanochannels. (i) As the molecules are driven from the input port to the output port in the nanochannel, they are observed using confocal fluorescence microscopy and detected using avalanche photodiodes. For this experiment, a 488 nm excitation laser was used since the DNA stain was YOYO-1.

Example 4

Imaging of Elongated DNA Obtained From a Small Collection of Cells and Maintained in the Chamber of a Microfluidic Device of the Present Invention Experiments have been conducted to use an embodiment of the microfluidic device of the present invention to trap a small collection of cells (in particular, 12 cells) and to extract DNA from these cells. Results are shown in FIG. 15.

Figure 15:
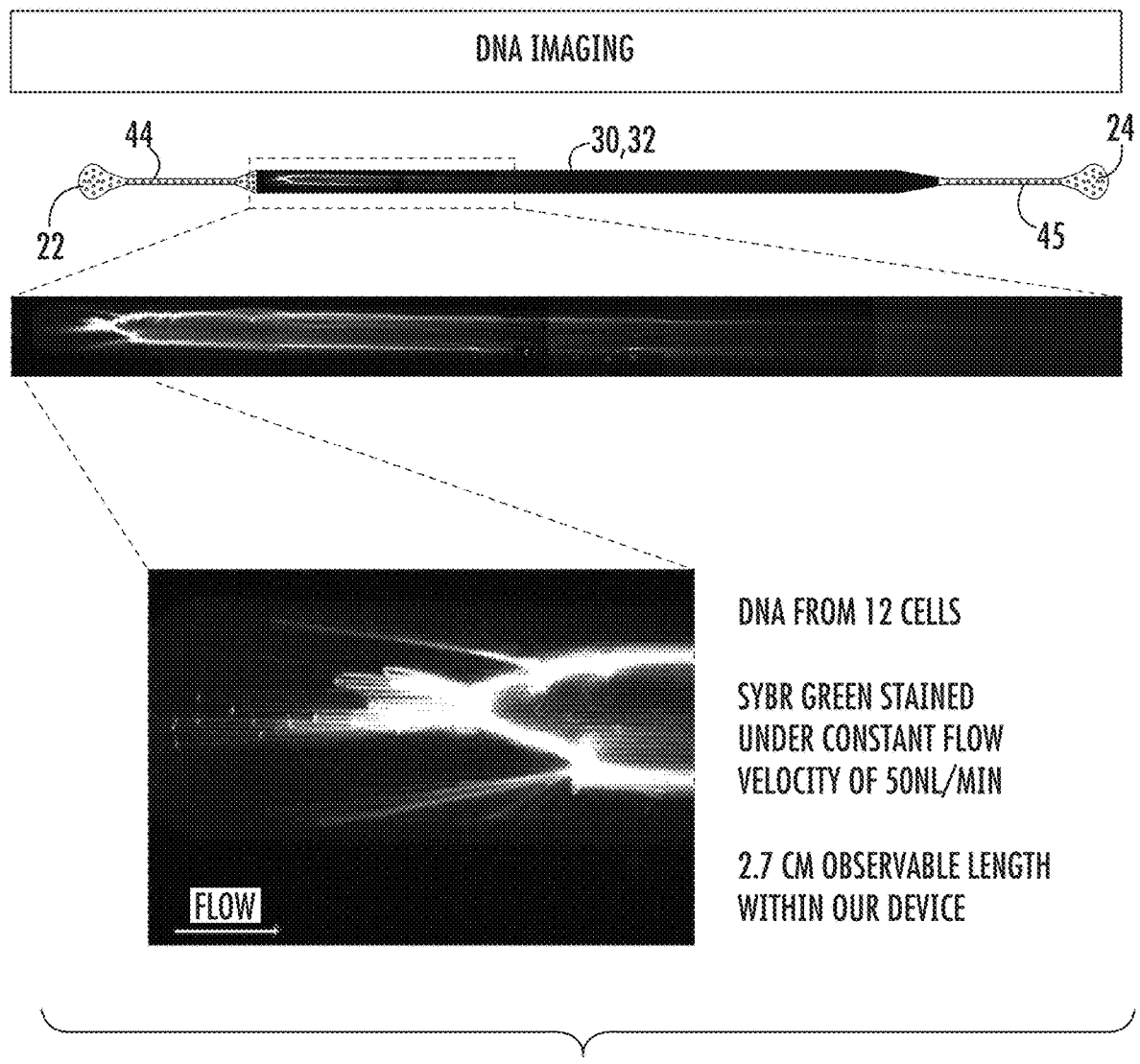
FIG. 15: A schematic of one embodiment of the microfluidic device of the present invention is shown (top portion). A micrograph of a section of the chamber of the microfluidic device that contains stained DNA from 12 cells is shown (middle portion). A close view of the beginning portion of the chamber of the microfluidic device that contains stained DNA from 12 cells is also shown (bottom left portion).

As can be seen from FIG. 15, the microfluidic device of the present invention can be used as a DNA imaging tool with the capabilities to elongate extracted DNA up to lengths that are orders of magnitude longer than current standards. DNA was extracted from 12 cells and stained with SYBR Green under constant flow velocity of 50 nl/minute. As shown in FIG. 15, the microfluidic device of the present invention was able to assist in elongating the extracted DNA. In this example, and as shown in FIG. 15, a composite image compiled from 18 micrographs was taken sequentially down the channel of the microfluidic device and representing a length of 1.1 cm out of the total observable 2.7 cm of DNA within that particular device. As shown in FIG. 15, DNA was inserted into microfluidic channel 30/chamber 32 through inlet port 22, with inflow channel 44 feeding into microfluidic channel 30/chamber 32. Liquid and other debris could then flow through outflow channel 45 and exit the device through outlet port 24.

REFERENCES

Citation of a reference herein shall not be construed as an admission that such reference is prior art to the present invention. All references cited herein are hereby incorporated by reference in their entirety. Below is a listing of various references cited herein:

A1. B. R. Cipriany, et al., "Single Molecule Epigenetic Analysis in a Nanofluidic Channel," *Analytical Chemistry*, vol. 82, pp. 2480-2487, March 2010.
A2. T. Yamamoto and T. Fujii, "Nanofluidic single-molecule sorting of DNA: a new concept in separation and analysis of biomolecules towards ultimate level performance," *Nanotechnology*, vol. 21, pp. 395502 (7 pp.)-395502 (7 pp.), 1 Oct. 2010.
A3. H. P. Chou, et al., "A microfabricated device for sizing and sorting DNA molecules," *Proceedings of the National Academy of Sciences of the United States of America*, vol. 96, pp. 11-13, January 1999.
A4. A. R. Wheeler, et al., "Microfluidic device for single-cell analysis," *Analytical Chemistry*, vol. 75, pp. 3581-3586, July 2003.
A5. Y. Tomizawa, et al., "Trapping probability analysis of a DNA trap using electric and hydrodrag force fields in tapered microchannels," *Phys Rev E Stat Nonlin Soft Matter Phys*, vol. 79, p. 051902, 2009 May (Epub 2009 May 2009.
A6. X. Chen, et al., "Continuous flow microfluidic device for cell separation, cell lysis and DNA purification," *Analytica Chimica Acta*, vol. 584, pp. 237-243, February 2007.
A7. J. Kim, et al., "Microfluidic sample preparation: cell lysis and nucleic acid purification," *Integrative Biology*, vol. 1, pp. 574-586, 2009.

A8. D. Irimia, et al., "Genome-wide transcriptome analysis of 150 cell samples," *Integrative Biology*, vol. 1, pp. 99-107, January 2009.

A9. D. Irimia, et al., "Single-cell chemical lysis in picoliter-scale closed volumes using a microfabricated device," *Analytical Chemistry*, vol. 76, pp. 6137-6143, October 2004.

A10. G. Ocvirk, et al., "beta-galactosidase assays of single-cell lysates on a microchip: A complementary method for enzymatic analysis of single cells," *Proceedings of the Ieee*, vol. 92, pp. 115-125, January 2004.

A11. E. A. Schilling, et al., "Cell lysis and protein extraction in a microfluidic device with detection by a fluorogenic enzyme assay," *Analytical Chemistry*, vol. 74, pp. 1798-1804, April 2002.

A12. R. N. Zare and S. Kim, "Microfluidic Platforms for Single-Cell Analysis," in *Annual Review of Biomedical Engineering*, Vol 12. vol. 12, ed Palo Alto: Annual Reviews, 2010, pp. 187-201.

A13. K. A. Wolfe, et al., "Toward a microchip-based solid-phase extraction method for isolation of nucleic acids," *Electrophoresis*, vol. 23, pp. 727-733, March 2002.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A system for analyzing DNA from a cell, the system comprising:
   a support comprising an inlet port;
   a microfluidic channel extending from the inlet port within the support;
   a micropillar array in the microfluidic channel, the micropillar array comprising:
      a first region of micropillars spatially configured to entrap a cell by size exclusion, and
      a second region of micropillars spatially configured to immobilize DNA that is released upon lysis of the cell entrapped in the first region of micropillars due to the DNA looping around said micropillars of the second region when hydrodynamic force is applied; and
   a fluorospectrometer or a fluorescent microscope operable to capture a fluorescent signal of the DNA released from the cell.

2. The system of claim 1, further comprising a nanofluidic component in fluid communication with an outlet port of the microfluidic channel, wherein an inlet port of said nanofluidic component isolates a single DNA molecule received from the microfluidic channel.

3. The system of claim 2, wherein the fluorospectrometer or the fluorescent microscope captures the fluorescent signal from the single DNA molecule at a time when the single DNA molecule flows through a nanochannel of the nanofluidic component.

4. The system of claim 2, wherein DNA molecules are driven electrophoretically through the microfluidic channel and/or the nanofluidic component.

5. The system of claim 2, wherein the microfluidic component is mounted to the nanofluidic component, such that the outlet port of the microfluidic channel empties into the inlet port the nanofluidic component.

6. The system of claim 2, wherein the microfluidic component is bonded to the nanofluidic component.

7. The system of claim 1, wherein the hydrodynamic force is applied to the microfluidic channel such that DNA released from lysed cells is immobilized in the micropillar array and cellular debris is washed away.

8. The system of claim 1, wherein the DNA is de-immobilized from the micropillar array by enzymatic digestion of the DNA with restriction endonucleases.

9. The system of claim 1, wherein the micropillar array comprises micropillars of one diameter in the first region and micropillars of a smaller diameter in the second region.

10. The system of claim 1, wherein the micropillar array comprises relatively widely spaced micropillars in the first region and more narrowly spaced micropillars in the second region.

* * * * *